(12) United States Patent
Mastrogiovanni et al.

(10) Patent No.: US 11,132,822 B2
(45) Date of Patent: *Sep. 28, 2021

(54) CUSTOM INTERFACE FOR CLIENT-SPECIFIC BEHAVIOR MODIFICATION

(71) Applicant: HEALTHVIEW SERVICES, INC., Danvers, MA (US)

(72) Inventors: Renato Ron Mastrogiovanni, Topsfield, MA (US); Zachary Shapleigh, Goffstown, NH (US); Amy Tenanes, Grafton, MA (US); Michael J. Gillen, Washington, MO (US); Raymond Weick, Eureka, MO (US)

(73) Assignee: HEALTHVIEW SERVICES, INC., Danvers, MA (US)

( * ) Notice: Subject to any disclaimer, the term of this patent is extended or adjusted under 35 U.S.C. 154(b) by 17 days.

This patent is subject to a terminal disclaimer.

(21) Appl. No.: 16/430,405

(22) Filed: Jun. 3, 2019

(65) Prior Publication Data

US 2019/0392620 A1    Dec. 26, 2019

Related U.S. Application Data

(63) Continuation-in-part of application No. 16/188,412, filed on Nov. 13, 2018, now Pat. No. 11,017,574,
(Continued)

(51) Int. Cl.
*G06T 11/60* (2006.01)
*A61B 3/10* (2006.01)
(Continued)

(52) U.S. Cl.
CPC .............. *G06T 11/60* (2013.01); *A61B 3/102* (2013.01); *G06Q 40/00* (2013.01); *G06Q 40/08* (2013.01)

(58) Field of Classification Search
CPC ........ G06Q 40/00; G06Q 40/08; A61B 3/102; G06T 11/60
(Continued)

(56) References Cited

U.S. PATENT DOCUMENTS 7,698,155 B1 * 4/2010 Prasad ................... G16H 70/40
705/3
7,702,527 B1 * 4/2010 Kron ....................... G16H 10/60
705/4
(Continued)

FOREIGN PATENT DOCUMENTS

CA          2734181 A1 *  2/2010  ............. G06Q 50/22
WO   WO-2007014307 A2 *  2/2007  ............. G16H 15/00

OTHER PUBLICATIONS

Baicker et al.: Workplace Wellness Programs Can Generate Savings, Feb. 2010, Health Affairs, Harvard University, pp. 1-8 (Year: 2010).*
(Continued)

*Primary Examiner* — Bijendra K Shrestha
(74) *Attorney, Agent, or Firm* — Troutman Pepper Hamilton Sanders LLP

(57) ABSTRACT

A financial management tool that includes calculated health care costs and health-based longevity to provide information to retirees to be able to calculate the amount of money that needs to be saved to cover retirement expenditures is provided with actual claims and actual related cost data from a database to increase the cost projection reliability of the tool.

23 Claims, 42 Drawing Sheets

Example 1
How Algorithms Are Applied

| To show calculation steps simply hover your mouse over any amount in blue. | | Medical (Individual) | Rx (Individual) | Medical (Emp-Based) | Rx (Emp-Based) | Dental | Docs/Tests Hosp | Rx | Dental | All Hearing | Vision |
|---|---|---|---|---|---|---|---|---|---|---|---|
| | Age 45 (2013) | $4,131.72 | $1,328.69 | $1,032.93 | $332.17 | $213.36 | $1,173.54 | $1,039.13 | $94.72 | $1.10 | $206.86 |
| 45 year-old male in Alabama Has poorly-managed Type 2 diabetes diagnosed within last year .. Full Detail >> Full Detail (ind covg) >> | Age 65 (2033) | $52,450.78 | $13,161.03 | $3,997.11 | $1,285.40 | $570.43 | $18,232.43 | $9,373.82 | $324.12 | $6.58 | $961.85 |
| | Age 71 (2039) (death by Type 2 Diabetes) | $109,237.50 | $24,099.66 | $5,996.58 | $1,929.04 | $78 | • Base Amount = $294.29 based on Diabetes Type2 managed poorly, diagnosed 0-1 years ago. • Trended forward 21 years at 7.00% = > $1,218.52. • Apply age/gender factor of 971.610% = > $11,839.24 • Apply disease management factor of 154.000% = > $18,232.43. • Apply years since diagnosis factor of 100.000% = > $18,232.43. | | | 74.15 |
| | Age 45 (2013) | $4,131.72 | $1,328.69 | $1,032.93 | $332.17 | $21 | | | | | 38.86 |
| 45 year-old male in Alabama Has well-managed Type 2 diabetes diagnosed within last year .. Full Detail >> Full Detail (ind covg) >>0 | Age 65 (2033) | $52,460.78 | $13,161.03 | $3,997.11 | $1,285.40 | $57 | | | | | 1.85 |
| | Age 80 (2048) (death by Type 2 Diabetes) | $264,959.20 | $56,298.04 | $11,028.15 | $3,546.46 | $1,192.69 | $51,027.44 | $19,124.26 | $689.78 | $23.39 | $3,105.65 |

Related U.S. Application Data which is a continuation of application No. 13/815,640, filed on Mar. 13, 2013, now Pat. No. 10,127,698.

(60) Provisional application No. 61/688,231, filed on May 10, 2012.

(51) Int. Cl.
*G06Q 40/00* (2012.01)
*G06Q 40/08* (2012.01)

(58) Field of Classification Search
USPC .......................................................... 705/35
See application file for complete search history.

(56) References Cited

U.S. PATENT DOCUMENTS

| | | | | |
|---|---|---|---|---|
| 7,711,619 | B2* | 5/2010 | Merton | G06Q 40/00 |
| | | | | 705/35 |
| 8,630,871 | B2* | 1/2014 | Rastogi | G06Q 40/08 |
| | | | | 705/2 |
| 2005/0202390 | A1* | 9/2005 | Allen | G09B 7/00 |
| | | | | 434/353 |
| 2005/0278196 | A1* | 12/2005 | Potarazu | G06Q 40/08 |
| | | | | 705/2 |
| 2007/0027727 | A1* | 2/2007 | Cochrane | G06Q 40/02 |
| | | | | 705/4 |
| 2007/0250427 | A1* | 10/2007 | Robinson | G06Q 40/06 |
| | | | | 705/36 R |
| 2008/0010086 | A1* | 1/2008 | Skelly | G06Q 40/02 |
| | | | | 705/2 |
| 2008/0133272 | A1* | 6/2008 | Marshall | G16H 50/20 |
| | | | | 705/3 |
| 2009/0192827 | A1* | 7/2009 | Andersen | G06Q 40/08 |
| | | | | 705/4 |
| 2010/0250277 | A1* | 9/2010 | Kuriyan | G16H 50/50 |
| | | | | 705/2 |
| 2012/0173398 | A1* | 7/2012 | Sjodin | G06Q 40/00 |
| | | | | 705/35 |
| 2013/0144642 | A1* | 6/2013 | Bessette | G06Q 10/10 |
| | | | | 705/2 |
| 2015/0262289 | A1* | 9/2015 | Hettesheimer | G06Q 40/00 |
| | | | | 705/35 |

OTHER PUBLICATIONS

McGrady et al.: Targeting Health Behaviors to Reduce Health Care Costs in Pediatric Psychology: Descriptive Review and Recommendations, Aug. 11, 2015, Journal of Pediatric Psychology, Oxford, 41(8), pp. 835-848 (Year: 2015).*

Medpac: Hospital Acute Inpatient Services Payment System, Payment Basics, Oct. 2009, pp. 1-5 (Year: 2009).*

* cited by examiner

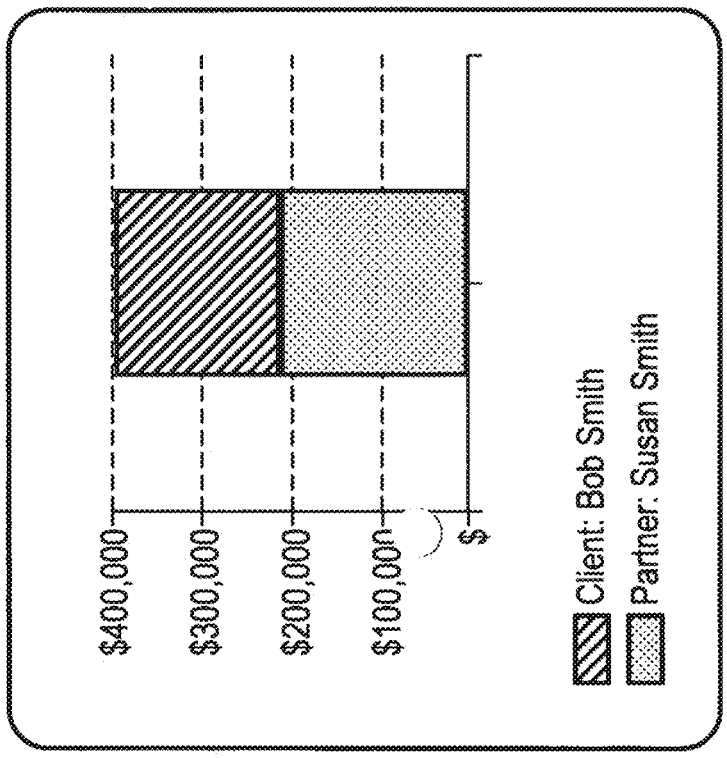
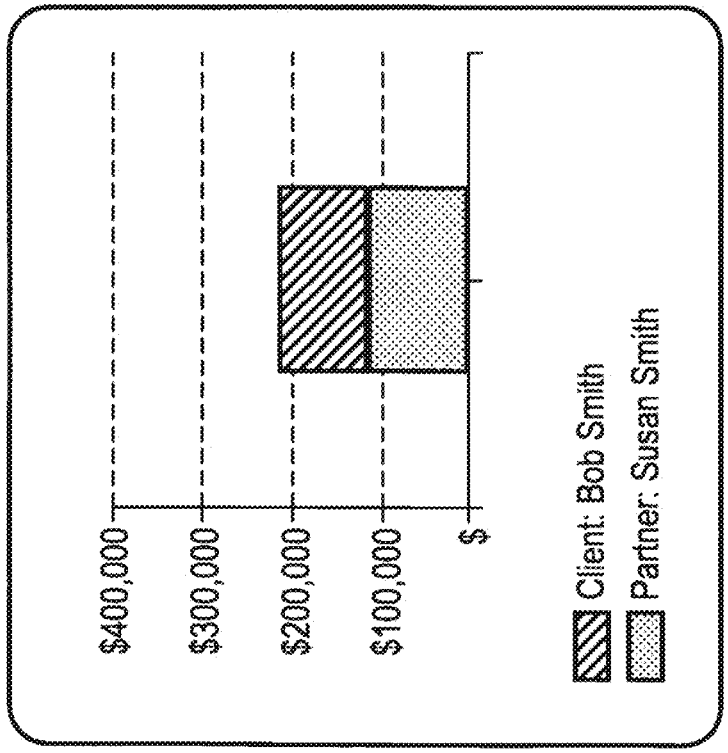
Fig. 8

Example 1
How Algorithms Are Applied

| To show calculation steps simply hover your mouse over any amount in blue. | | Medical (Individual) | Rx (Individual) | Medical (Emp-Based) | Rx (Emp-Based) | Dental | Docs/Tests Hosp | Rx | Dental | All Hearing | Vision |
|---|---|---|---|---|---|---|---|---|---|---|---|
| 45 year-old male in Alabama Has poorly-managed Type 2 diabetes diagnosed within last year... Full Detail >> Full Detail (ind covg) >> | Age 45 (2013) | $4,131.72 | $1,328.69 | $1,032.93 | $332.17 | $213.36 | $1,173.54 | $1,039.13 | $94.72 | $1.10 | $206.86 |
| | Age 65 (2033) | $52,450.78 | $13,161.03 | $3,997.11 | $1,285.40 | $570.40 | $18,232.43 | $9,373.82 | $324.12 | $6.59 | $961.85 |
| | Age 71 (2039) (death by Type 2 Diabetes) | $109,237.50 | $24,099.66 | $5,998.58 | $1,929.04 | $76 | | | | | $74.15 |
| 45 year-old male in Alabama Has well-managed Type 2 diabetes diagnosed within last year... Full Detail >> Full Detail (ind covg) >>0 | Age 45 (2013) | $4,131.72 | $1,328.69 | $1,032.93 | $332.17 | $21 | | | | | $6.86 |
| | Age 65 (2033) | $52,450.78 | $13,161.03 | $3,997.11 | $1,285.40 | $57 | | | | | $1.85 |
| | Age 80 (2048) (death by Type 2 Diabetes) | $284,959.20 | $55,298.04 | $11,028.15 | $3,546.46 | $1,192.69 | $51,027.44 | $19,124.26 | $689.70 | $23.39 | $3,105.65 |

Callout (on Age 65 row, Docs/Tests Hosp $18,232.43):
- Base Amount = $294.29 based on Diabetes Type2 managed poorly, diagnosed 0-1 years ago.
- Trended forward 21 years at 7.00% = > $1,218.52.
- Apply age/gender factor of 971.610% = > $11,839.24
- Apply disease management factor of 154.000% = > $18,232.43.
- Apply years since diagnosis factor of 100.000% = > $18,232.43.

General

Date of birth: 01/01/1983 — 1401

Gender: ○ Female  ● Male — 1402

Race: Caucasian — 1403

Height: 6 ft / 0 in — 1404

Weight: 195 lbs — 1405

Cancel

Blood Pressure

Do you have or have you been told that you have high blood pressure?
- ● Yes  ○ No — 1601

Does/did your mother, father, brother, or sister have high blood pressure?
- ● Yes  ○ No — 1602

Do you know your blood pressure?
- ● Yes  ○ No — 1603

Blood Pressure:
[ 130 ] / [ 80 ] mm Hg (eg: 120/80) — 1604

How many medications have you been prescribed to manage your blood pressure?
- ○ Zero  ● One  ○ Two or More — 1605

Do you always take your medications as prescribed?
- ● Yes  ○ No — 1606

How often do you have a drink containing alcohol
- ○ Never
- ○ A few times a month — 1607
- ● Daily or almost daily How many drinks containing alcohol do you have on a typical day when you are drinking?
- ● One
- ○ Two — 1608
- ○ More than two Is your diet high in salt?
- ● Yes  ○ No — 1609

Is your diet high in potassium?
- ○ Yes  ● No — 1610

Is your diet high in vitamin D?
- ● Yes  ○ No — 1611

[ Submit ]  [ Cancel ]

Diabetes

Do you have or have you been told that you have type II diabetes or high blood sugar (prediabetes)?
○ Yes  ○ No
— 1701

Do you have?
○ Type II Diabetes
○ Prediabetes
— 1702

Do you use insulin?
○ Yes  ○ No
— 1703

Do you have your A1c value?
○ Yes  ○ No
— 1704

A1c: [ 8.0 ]  %  Normal < 5.7%

Do you have your Fasting Blood Sugar value?
— 1705
○ Yes  ○ No
— 1706

Fasting Blood Sugar: [ 8.7 ]  mg/dL  Average 100 - 300 mg/dL
— 1707

Other than insulin, how many medications have you been prescribed to manage your diabetes and/or blood sugar?
○ None  ○ One  ○ Two or More
— 1708

Do you always follow a diabetic diet?
○ Yes  ○ No
— 1709

Do you attend all of your recommended doctors appointments?
○ Yes  ○ No
— 1710

Does/did your mother, father, brother, or sister have diabetes?
○ Yes  ○ No
— 1711

[ OK ]  [ Cancel ]

Cholesterol

Has a medical professional ever told you that you are at risk of having high cholesterol?
○ Yes  ○ No ——— 1801

Do you or have you been told that you have high cholesterol?
○ Yes  ○ No ——— 1802

Does/did your father or brother have heart disease (before age 55)?
○ Yes  ○ No ——— 1803

Does/did your mother or sister have heart disease (before age 65)?
○ Yes  ○ No ——— 1804

Do you know your cholesterol reading?
○ Yes  ○ No ——— 1805

LDL: [100]    mg/dL  Average < 100 mg/dL ——— 1806

HDL: [62]    mg/dL  Average < 60 mg/dL ——— 1807

Total: [215]  mg/dL  Average < 200 mg/dL ——— 1808

Are you on cholesterol medication or have you been on cholesterol medication in the past?
○ Yes  ○ No ——— 1809

Do you have a waist circumference of at least 40 inches (102 centimeters)?
○ Yes  ○ No ——— 1810

Do you eat many bad fats?
○ Yes  ○ No ——— 1811 ——— 1813

Do you eat many good fats?
○ Yes  ○ No ——— 1812

[OK] [Cancel]

Weight

What was your highest adult weight?

[ 220 ] —— 1901

Age at this weight?

[ 25 ] —— 1902

Does/did your mother, father, brother, or sister suffer from obesity?
- ○ Yes  ● No —— 1903

How often do you exercise? ⓘ
- ○ Not at all —— 1904
- ○ At least 150 minutes (2.5 hours) per week of moderate-intensity cardio activity
- ○ At least 75 minutes (1.25 hours) per week of vigorous-intensity cardio activity
- ○ An equivalent combination of moderate- and vigorous-intensity cardio activity (ie: 75 minutes of moderate-intensity activity and 37 minutes of moderate cardio activity)
- ● Some, but less than the previous options Please describe your eating habits. (Select all that apply.) —— 1905
- ☐ I eat meals quickly.
- ☐ I often eat even when I'm not hungry.
- ☐ I often eat sweets/desserts. ⓘ

[ Save ]  [ Cancel ]

FIG. 19

HIGH BLOOD PRESSURE/HYPERTENSION

POTENTIAL BEHAVIOR MODIFICATIONS:
<u>BETTER:</u>
[Continue to] Limit salt Intake
[Continue to] take your medications as directed
<u>BEST:</u>
[Continue to] Limit salt Intake
[/Continue your current] Increase your physical activity
Drink in moderation

BETTER:

[Continue to] Limit salt Intake

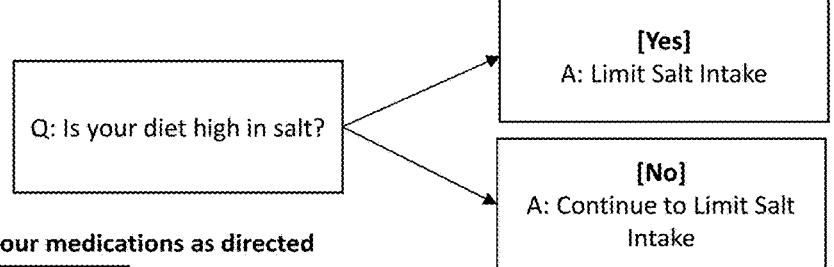

[Continue to] take your medications as directed

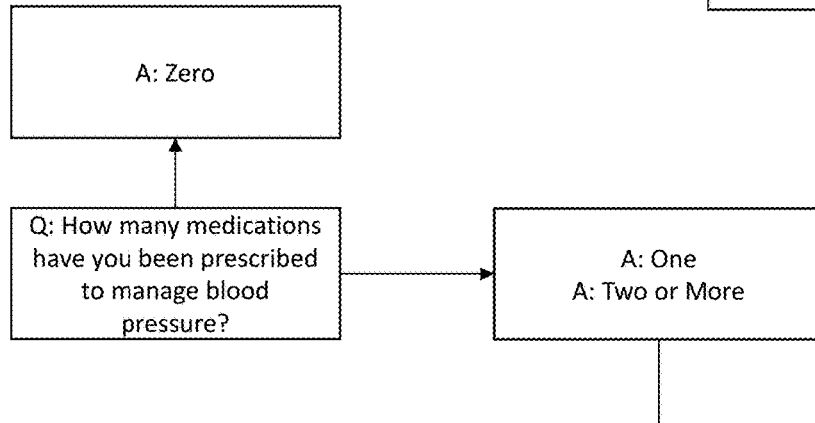

FIG.22

HIGH BLOOD PRESSURE/HYPERTENSION CON'T
BEST:
[Continue to] Limit salt Intake
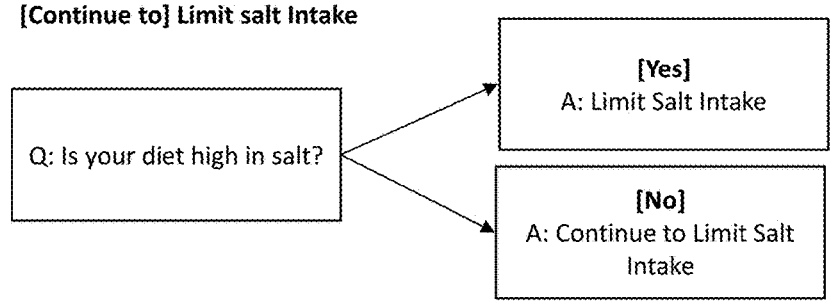
[Continue your current level of/] Increase your physical activity
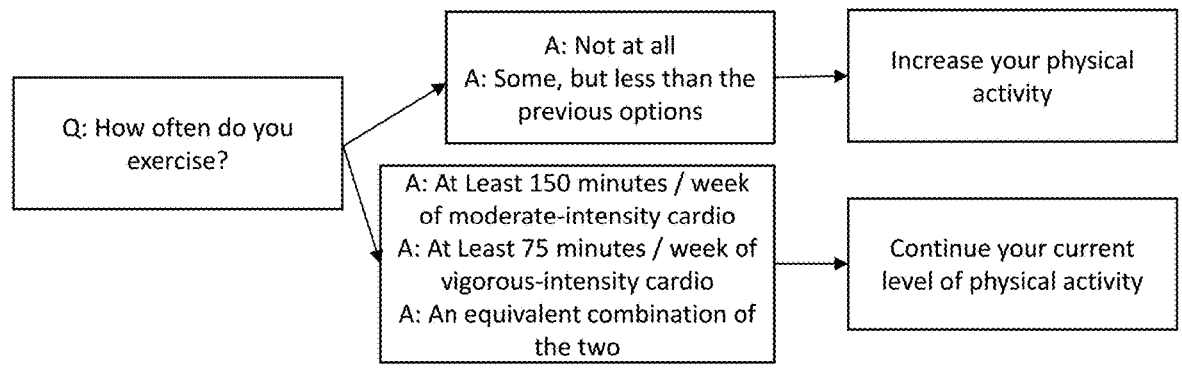
[Continue to] Drink in moderation
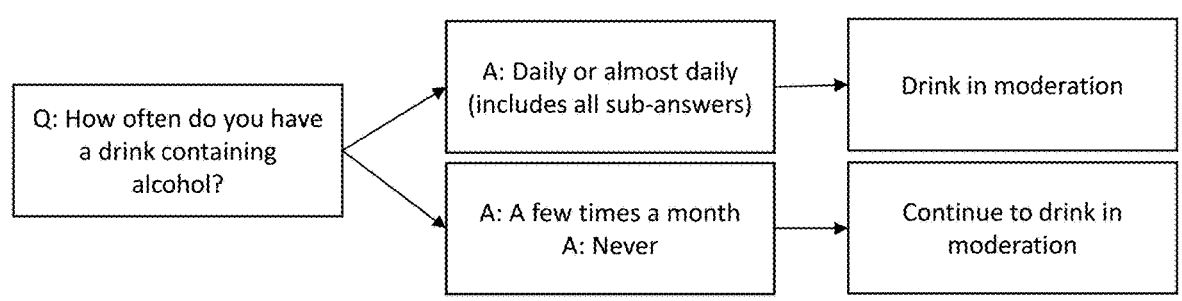
FIG. 23

| DIABETES |
|---|

> POTENTIAL BEHAVIOR MODIFICATIONS:
> BETTER:
> [Continue to/] Follow a diabetic diet.
> [Continue to/] Monitor your symptoms and attend your recommended doctors appointments.
> [Continue to/] Take your medicines are prescribed.
> BEST:
> [Continue to/] Follow a diabetic diet.
> [Continue to/] Monitor your symptoms and attend your recommended doctors appointments.
> [Continue to/] Take your medicines are prescribed.
> [Continue your current level of/Increase your] physical activity

BEST:
[Continue to/] Follow a diabetic diet.

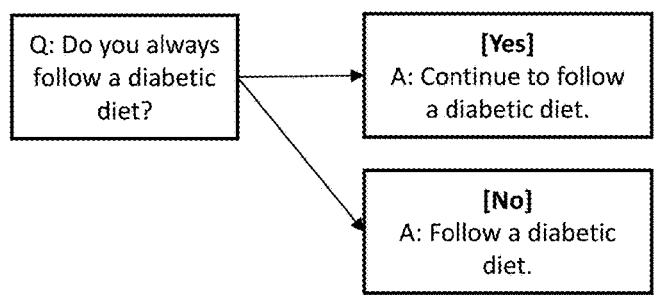

[Continue to/] Monitor your symptoms and attend your recommended doctor's appointments

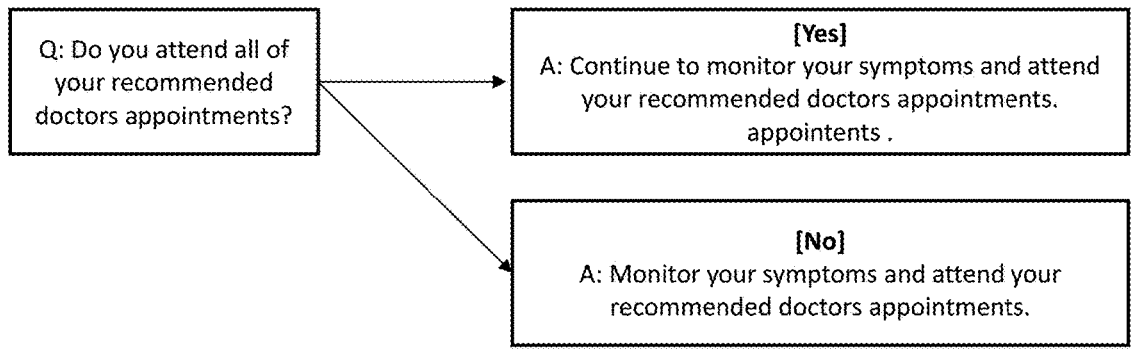

FIG. 24

DIABETES CON'T
[Continue to] Take your medications as prescribed.
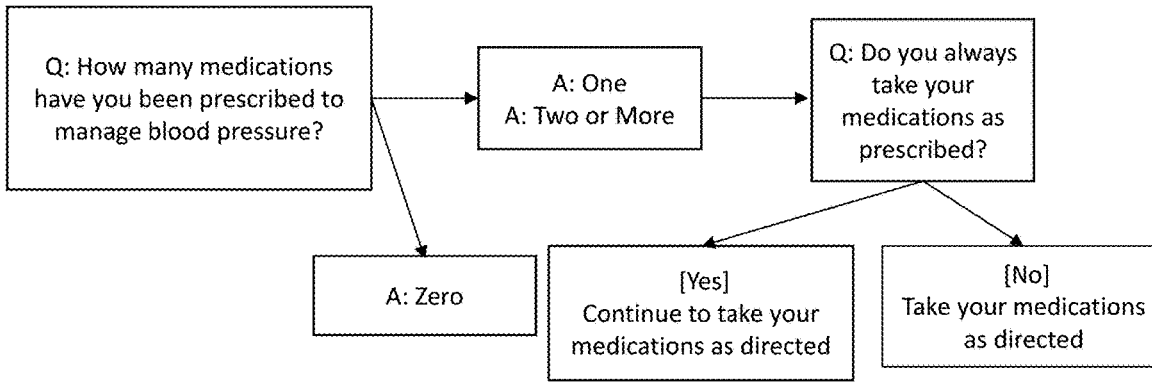
[Continue your current level of/] Increase your physical activity.
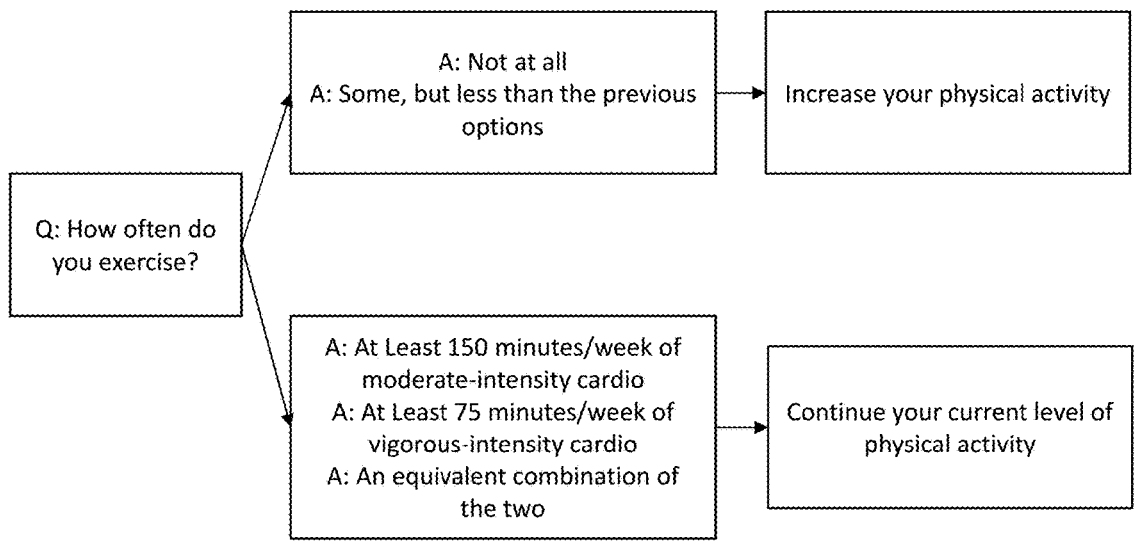
FIG. 25

| HIGH CHOLESTEROL |
|---|

POTENTIAL BEHAVIOR MODIFICATIONS:
BETTER:
[Continue to/] Choose healthy fats.
[Continue to/] Take your medications as prescribed.
BEST:
[Continue to/] Choose healthy fats.
[Continue to/] Take your medications as prescribed.
[Continue to/] Limit Salt Intake
[Continue to/] Continue your current level of physical activity BETTER:
[Continue to/] Choose healthy fats

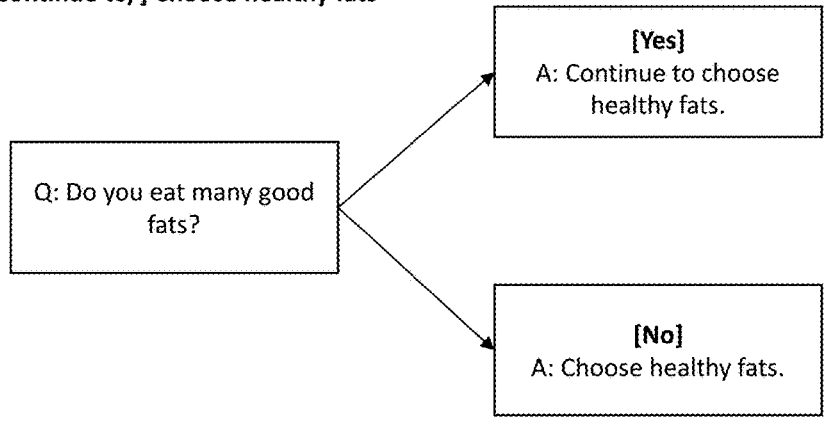

Continue to take your medications as prescribed

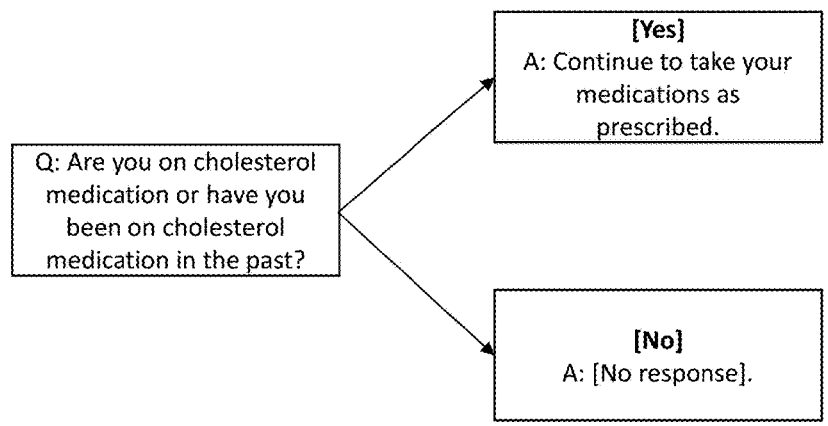

FIG. 26

HIGH CHOLESTEROL CON'T

BEST:

[Continue to/] Choose healthy fats

Q: Do you eat many good fats?
- [Yes] A: Continue to choose healthy fats.
- [No] A: Choose healthy fats.

[Continue to] Take your medications as prescribed

Q: Are you on cholesterol medication or have you been on cholesterol medication in the past?
- [Yes] A: Continue to take your medications as prescribed.
- [No] A: [No response].

[Continue to] Limit salt intake.

Q: Is your diet high in salt?
- [Yes] A: Limit Salt Intake
- [No] A: Continue to Limit Salt Intake

Please complete the below questionnaire.

We will help to assess your risk preference and then invest the money for you, depending on that risk preference.

What is your financial goal for this portfolio?
[ Finance Retirement ⬍ ] —— 3501

Describe your level of investment experience and knowledge:
[ None ⬍ ] —— 3502

How long have you been investing?
[ Never ⬍ ] —— 3503

How long do you plan to invest this money?
[ Greater than 15 years ⬍ ] —— 3504

Which of the following statements most accurately describe your tolerance for risk?
[ I am willing to accept negative returns from time to time to achieve my long-term investment goals ⬍ ] —— 3505

How long until you plan on withdrawing money from this account?
[ Greater than 15 years ⬍ ] —— 3506

If you needed $10,000 due to an unexpected financial obligation, would you need to redeem this money from your account?
◯ Yes  ⦿ No —— 3507

CUSTOM INTERFACE FOR CLIENT-SPECIFIC BEHAVIOR MODIFICATION

CROSS-REFERENCE TO RELATED APPLICATIONS

This application is a continuation in part of U.S. patent application Ser. No. 16/188,412 entitled, "METHOD, APPARATUS AND SYSTEM FOR FINANCIAL PLANNING INCORPORATING CALCULATED HEALTH COSTS BASED ON ACTUAL CLAIMS AND THE ACTUAL COST THEREOF" filed Nov. 13, 2018, which is a continuation of U.S. patent application Ser. No. 13/815,640 entitled "METHOD, APPARATUS AND SYSTEM FOR FINANCIAL PLANNING INCORPORATING CALCULATED HEALTH COSTS BASED ON ACTUAL CLAIMS AND THE ACTUAL COST THEREOF" filed Mar. 13, 2013, which claims benefit of U.S. Provisional Application No. 61/688,231, entitled "METHOD, APPARATUS AND SYSTEM FOR FINANCIAL PLANNING INCORPORATING CALCULATED HEALTH COSTS BASED ON ACTUAL CLAIMS AND THE ACTUAL COST THEREOF" filed May 10, 2012, all of which are hereby incorporated by reference in their entirety.

BACKGROUND

In the financial planning process, financial services are available from a large number of companies include comprehensive planning tools that aid individuals in planning for retirement. These comprehensive planning tools provides an individual with ways of planning for the individual's retirement based on the individual's personal financial profile. Typically these comprehensive planning tools take into account contributing factors, such as fixed and variable living expenses such as mortgage, food, utilities, clothing, vacation expenses, charity donations, and taxes. Typically these tools specify a retirement date and project available funds by taking into account various income sources as well as expenses throughout the retirement period.

These comprehensive tools may factor in retirement income generated from sources such as savings, Social Security, a pension, veteran's benefits as well as employment during retirement.

All of these comprehensive tools project available cash or income while making adjustments for variables such as inflation and the rate of return, allowing an investment counselor to determine the financial status of their client.

The problem with such comprehensive planning tools is that they fail to take into account out-of-pocket health care costs and expected longevity based on a personal health profile for each individual. Up until the present time, there has been no way of calculating an investor's future out of pocket health care costs based on a customized personal medical profile and expected lifespan. Because medical expenses are the largest expense that Americans will face in retirement, it is critically important that financial planners have an accurate and consistent means of incorporating health care expenses and life span into the retirement planning process. Moreover, traditional retirement planning tools do not incorporate longevity statistics based on the health of the individual.

Thus, in the past there has not been a retirement planning tool that incorporates into individual plans personalized actuarial based longevity, as well as a calculation of health care expenses based on the health of the individual.

BRIEF DESCRIPTION OF DRAWINGS

FIG. 8 is a diagrammatic illustration of the estimated medical costs in retirement, which compares savings needed to cover medical expenses in retirement versus actual medical expenses in retirement.

FIG. 12 is a healthcare centric chart for deriving an age-appropriate hospital cost based on the actual claims and actual cost database of FIG. 10.

FIG. 13 depicts a dashboard of a website in accordance with an embodiment.

FIG. 14 depicts a general questionnaire as part of a health profile in accordance with an embodiment.

FIG. 16 depicts a blood pressure questionnaire as part of a health profile in accordance with an embodiment.

FIG. 17 depicts a diabetes questionnaire as part of a health profile in accordance with an embodiment.

FIG. 18 depicts a cholesterol questionnaire as part of a health profile in accordance with an embodiment.

FIG. 19 depicts a weight questionnaire as part of a health profile in accordance with an embodiment.

FIG. 22 depicts a flowchart of potential behavior modifications relating to high blood pressure or hypertension based on user input in accordance with an embodiment.

FIG. 23 depicts a continuation of the flowchart of potential behavior modifications relating to high blood pressure or hypertension based on user input in accordance with an embodiment.

FIG. 24 depicts a flowchart of potential behavior modifications relating to diabetes based on user input in accordance with an embodiment.

FIG. 25 depicts a continuation of the flowchart of potential behavior modifications relating to diabetes based on user input in accordance with an embodiment.

FIG. 26 depicts a flowchart of potential behavior modifications relating to high cholesterol based on user input in accordance with an embodiment.

FIG. 27 depicts a continuation of the flowchart of potential behavior modifications relating to high cholesterol based on user input in accordance with an embodiment.

FIG. 34 depicts investment assistance based on the healthcare cost projections in accordance with another embodiment.

FIG. 35 depicts investment assistance based on the healthcare cost projections in accordance with another embodiment.

FIG. 37 depicts investment assistance based on the healthcare cost projections in accordance with another embodiment.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Figure 1:
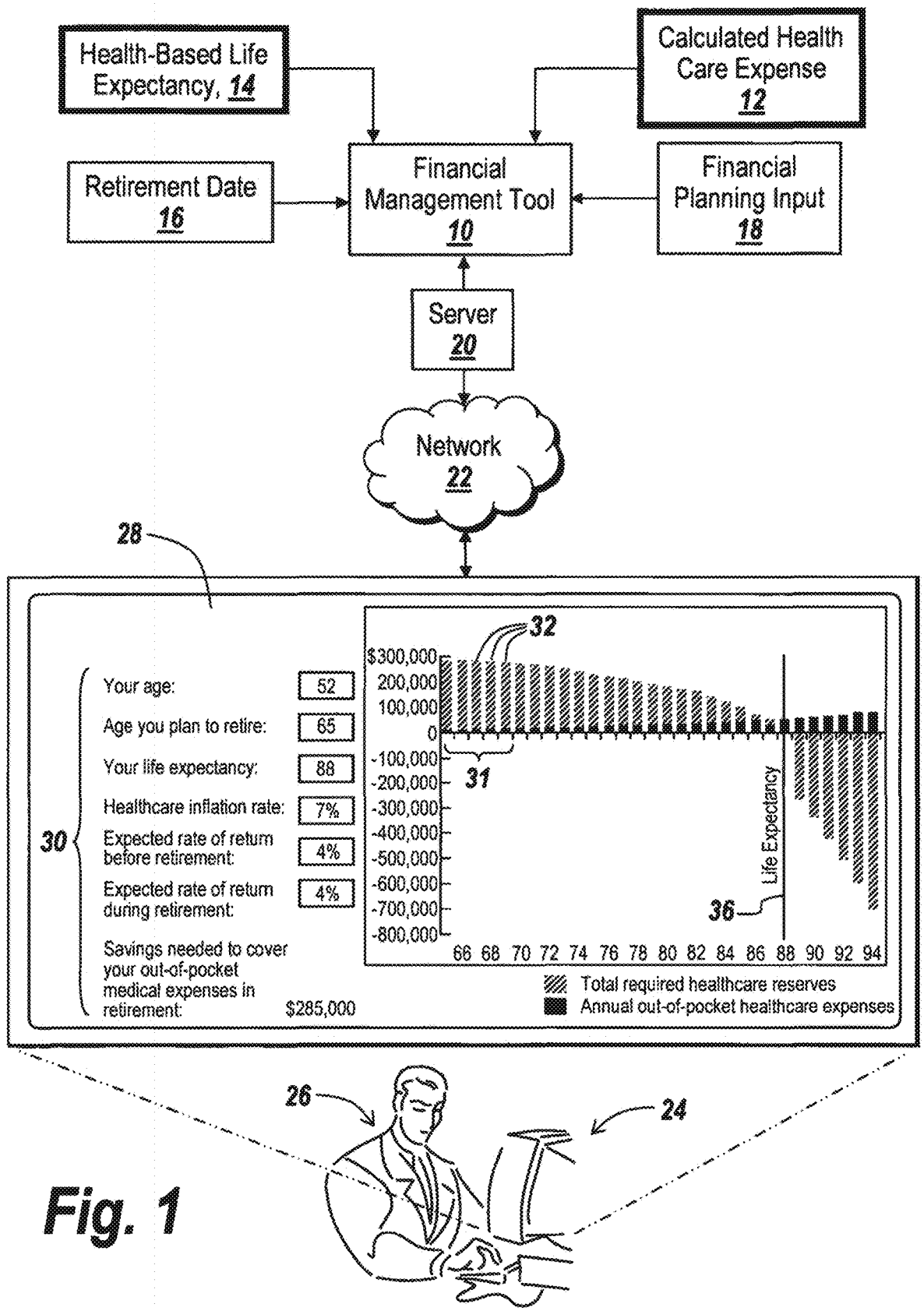
FIG. 1 is a diagrammatic illustration of the subject financial management tool utilizing health-based life expectancy and calculated health care expense to provide a display of cost of living versus available assets.

Referring now to FIG. 1, a financial management tool 10 is provided according to an embodiment with both calculated health care expense 12 and health-based life expectancy 14. The tool 10 may take into account health-based information to assist in financial management during retirement. Additional inputs to the financial management tool may include a selected retirement date 16 and financial planning input 18 that includes expected state of residence, expected income in retirement, current savings and current and future rates of returns. The financial management tool may incorporate a processor for running algorithms that provides the calculations necessary for the subject invention including income and state of residency, as well as data storage.

The financial management tool 10 is coupled by a server 20 to a network 22 that may include the internet or some wireless communications network. Input to the financial management tool may be through a terminal 24 operated by an individual 26. Here, the terminal 24 has a display 28 and enables input of relevant individual data in fields in the tool's data storage. The display of health-related information enables the individual to plan for retirement.

As can be seen on display 28, a number of fields 30 may respectively relate to the age of the individual, the age that the individual plans to retire, the calculated life expectancy of the individual, the health care inflation rate, the expected rate of return before retirement, and the respected rate of return during retirement.

As a result of the operation of the tool, the savings needed to cover the out-of-pocket medical expense portion of the expenses associated with retirement may be calculated.

The graph to the right of the display are the out-of-pocket medical expenses per year in retirement based on the information that has been provided in the dialog boxes to the left.

Assuming that an amount of savings needed to cover out-of-pocket medical expenses in retirement for a person age 52 that plans to retire at 65 and has a life expectancy of 88, what is displayed by columns 32 are the total required health care reserves. The shaded portions 34 show the annual out-of-pocket health care expenses. It is noted that the life expectancy 36 is derived based on not only average actuarial tables, but also actuarial tables taking into account the particular individual's health status.

As can be seen at age 65, in one example the amount of assets available is $285,000. This sum is decreased by the total required health care cost, with the out-of-pocket health care expenses increasing during the retirement years. What can be clearly seen from this chart is that the health care reserves are completely depleted at the calculated date of death.

Thus, the chart indicates that given all the health care information incorporated into the calculation, at the time of death one has completely depleted one's health care reserves. This is based upon initial savings, the health care inflation rate, the expected rate of return before retirement, and the expected rate of return during retirement.

This tool can be exercised by the individual by selecting values for the indicated variables, such as to compare the financial implications of retiring at one age as opposed to another.

One can also evaluate one's financial situation by varying the rates of return, both post-retirement and pre-retirement.

Figure 2:
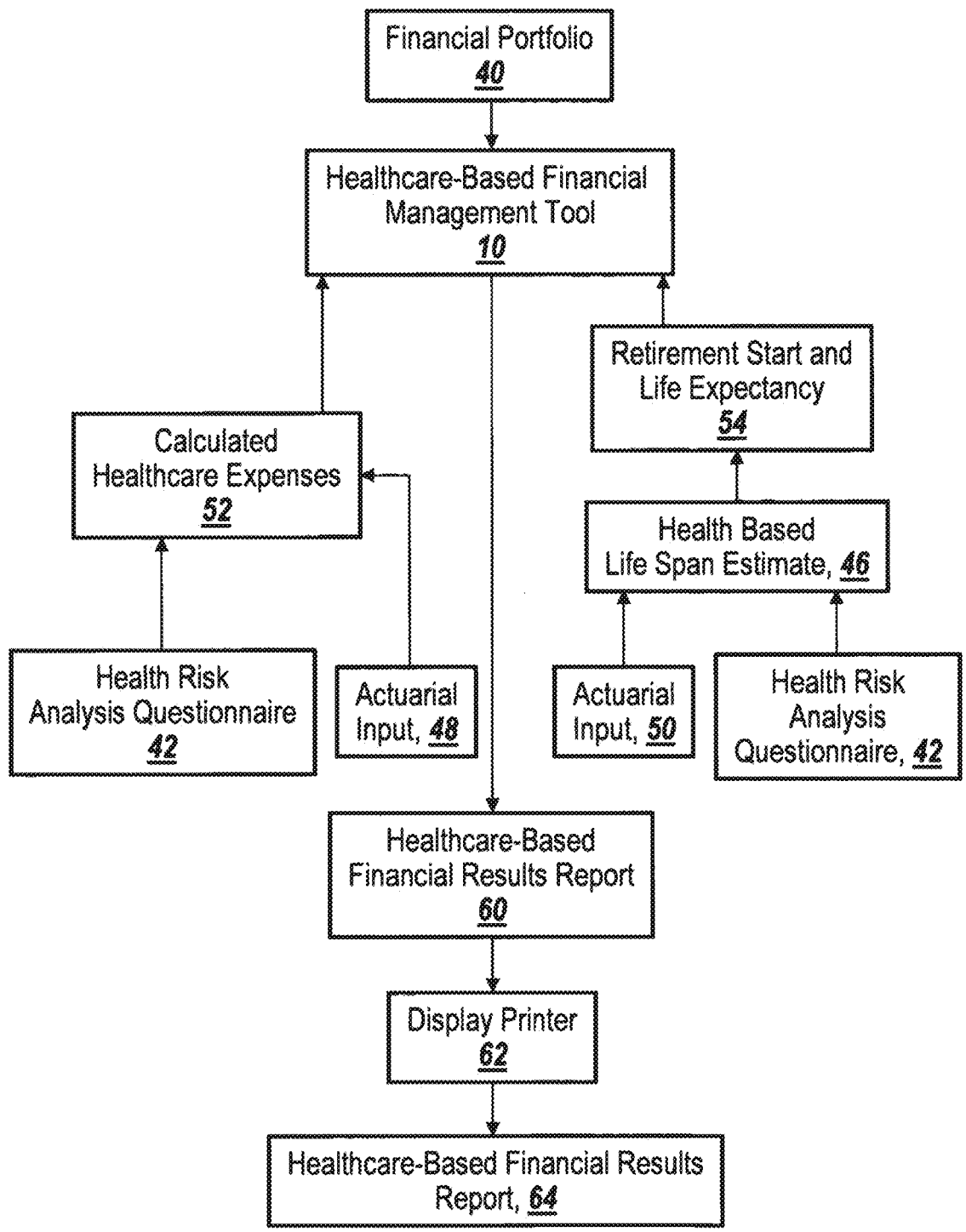
FIG. 2 is a block diagram of the system of FIG. 1 in which the results of a health risk analysis questionnaire are provided to project health care costs and to provide health-based lifespan estimates.

Referring to FIG. 2, the financial management tool 10 includes a financial planning input from a financial portfolio 40 in which various investment portfolio scenarios can be entered into the tool 10. With respect to this financial planning tool, health care based initiative engendered by the completion of the health risk analysis questionnaire 42, which is used both to provide information about and to project health care costs as illustrated at 44, and to deliver a health-based life plan estimate 46. An actuarial input 48 may be used to enable the projected health care costs to be calculated 52. A separate actuarial input 50 may be able to provide for a health-based life span estimate.

The projected health care costs are the health care expenses calculated at 52, whereas the health-based life span estimate 46 is utilized to populate a module 54 that defines the retirement start date and the life expectancy of the individual.

As shown, a health care based financial results report 60 is supplied to a display or printer 62 from which health care based financial reports can be viewed as illustrated at 64.

Figure 3:
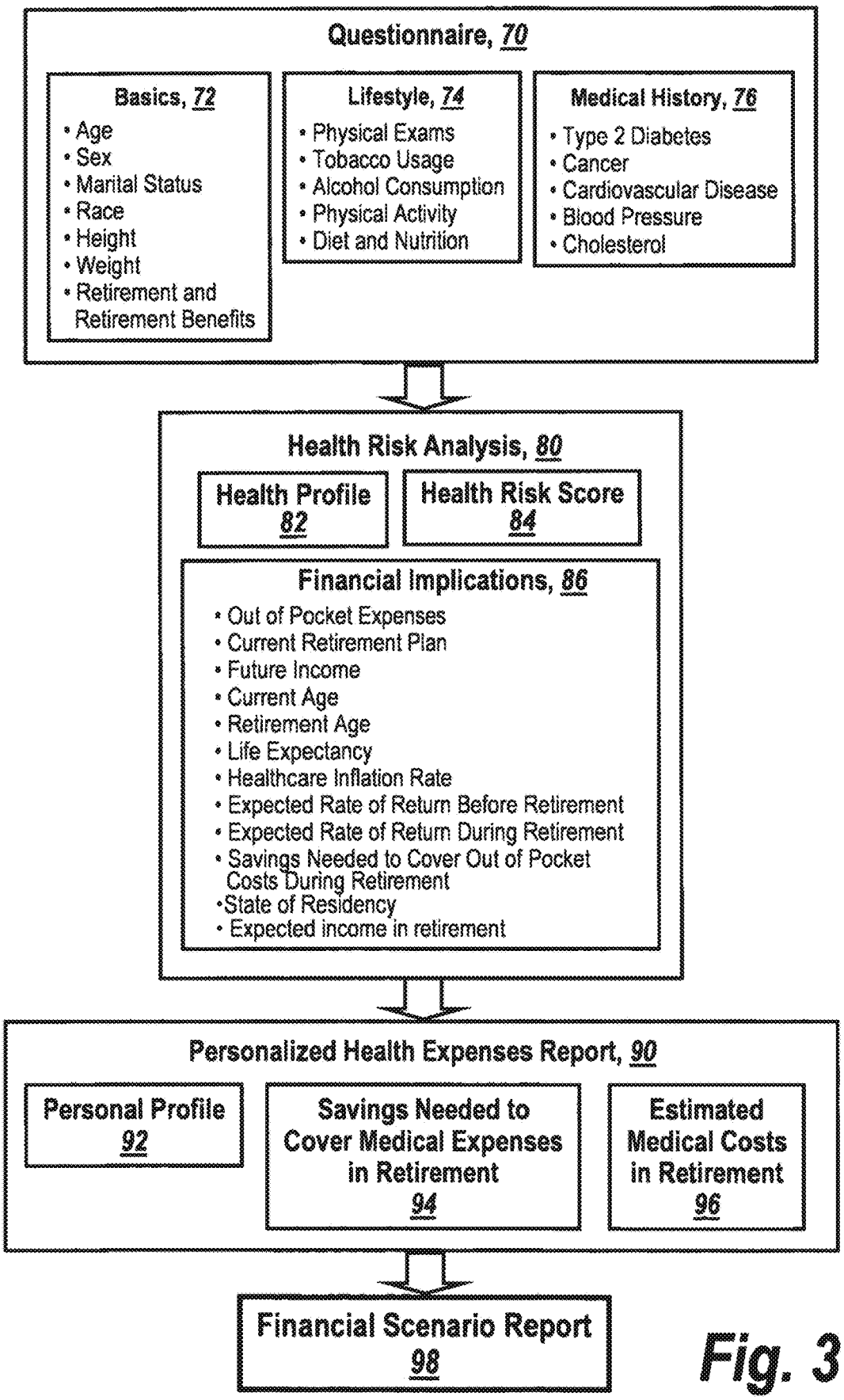
FIG. 3 is a diagrammatic illustration of the health care questionnaire utilized in the subject invention, which incorporates basic information about the individual, lifestyle and medical history to provide a health risk analysis that results in a personalized health expense financial management tool that calculates the savings or income needed to cover out-of-pocket costs during retirement.

Another element of the financial management tool is the health care questionnaire shown in FIG. 3, designated by reference character 70. Here the health care questionnaire 72 incorporates basic information such as age, sex, marital status, race, height, weight and answers to types of retirement plans and retirement benefits. The questionnaire also includes a lifestyles portion 74 that incorporates the result of physical exams, tobacco usage, alcohol consumption, physical activity, and diet and nutrition. Further, the questionnaire also includes a medical history section 76 that includes medical indicators, such as type 2 diabetes, cancer, cardiovascular disease, blood pressure, and cholesterol numbers.

The result of the questionnaire is applied to a health risk analysis module 80 that includes a health profile 82 generated from questionnaire 70, as well as a health risk score 84.

The health risk analysis identifies the financial implications 86 for entry into a financial plan such as out-of-pocket health care expenses.

Once the health risk analysis module 80 has calculated the various financial implications, the module outputs a personalized health expenses report 90, which includes a personal profile 92, the savings needed to cover medical expenses in retirement 94, and the estimated medical costs in retirement 96. These implications are contained in a final financial scenario report 98.

It is thus important for the individual planning for retirement to be able to know what amount to set aside for retirement by taking into account not only the usual financial analysis tool outputs, but also modification of these outputs that account for the health of the individual.

Figure 4:
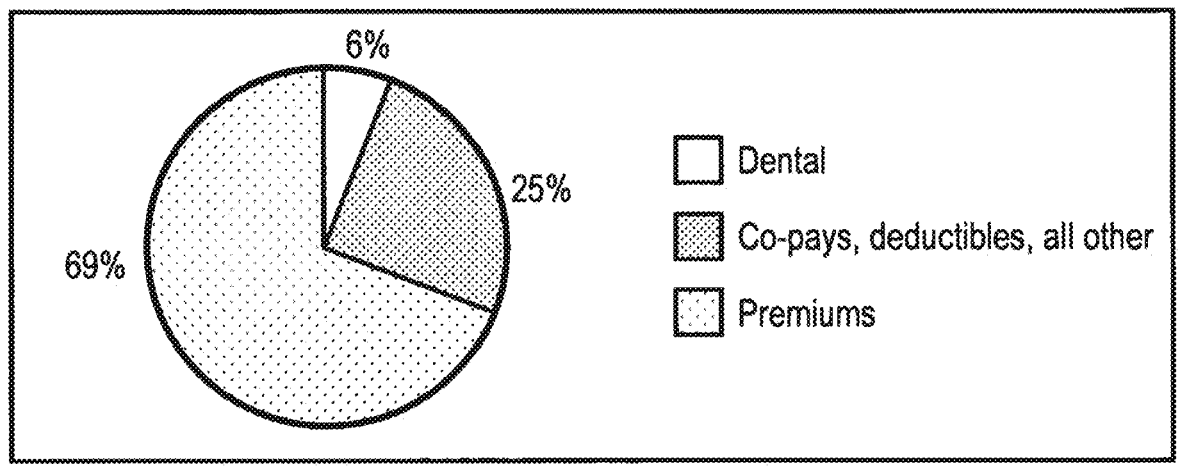
FIG. 4 is a pie chart showing projected out-of-pocket health care expenses broken up into dental, co-pays and premiums.

Referring to FIG. 4 the pie chart identifies that projected out-of-pocket health care expenses for an individual are 69% due to premiums, 25% due to co-pays, deductibles and all other expenses, and about 6% due to dental costs. These values are merely exemplary and are thus non-limiting in nature.

Figure 5:
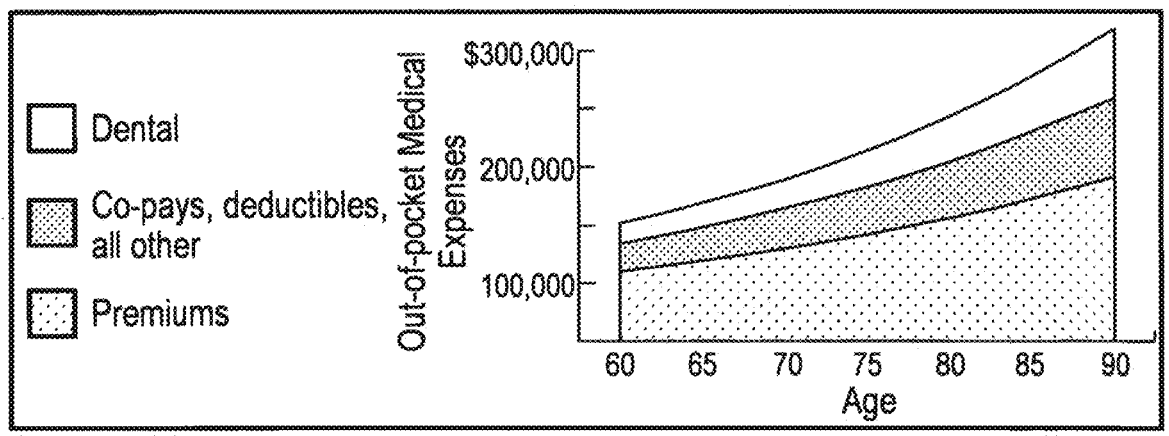
FIG. 5 is a graph showing expense growth over the course of retirement years for dental, co-pays and premiums.

Referring to FIG. 5, projected health care expenses may grow over the course of one's retirement years. For example, the combined dental, co-pay and premium cost at for instance age 60 of $150,000 may increase to over $300,000 if the individual lives to the age of 90.

Figure 6:
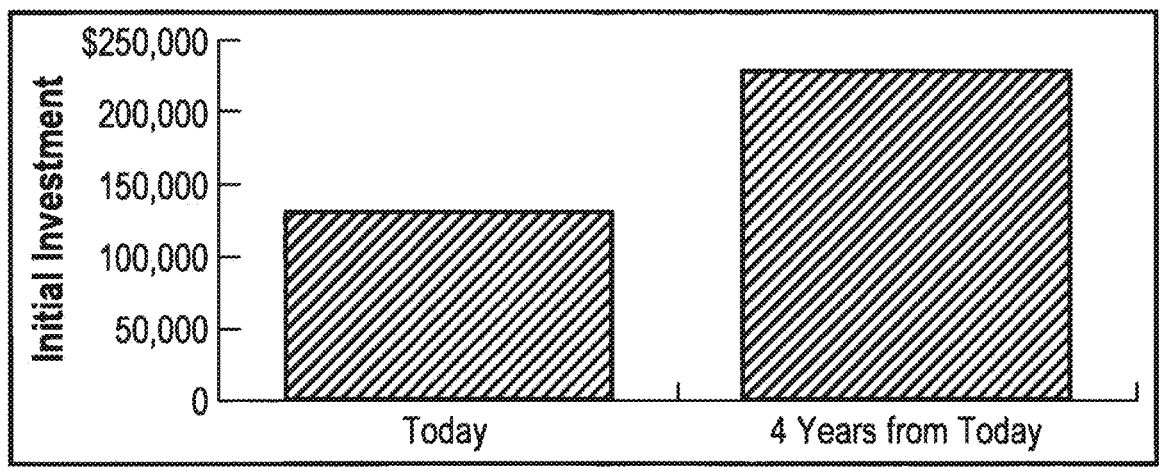
FIG. 6 is a graph showing the cost of waiting to enter into a retirement program based on current assets available versus costs in four years.

Another useful output of the financial management tool is calculating the cost effect of waiting for retirement. As can be seen by the graph in FIG. 6, assuming that one has a current health care cost of $140,000, it can be seen through the use of the subject tool that waiting for 4 years to begin retirement would result in an overall cost increase to approximately $250,000, showing that delay in retirement planning is indeed costly.

Figure 7:
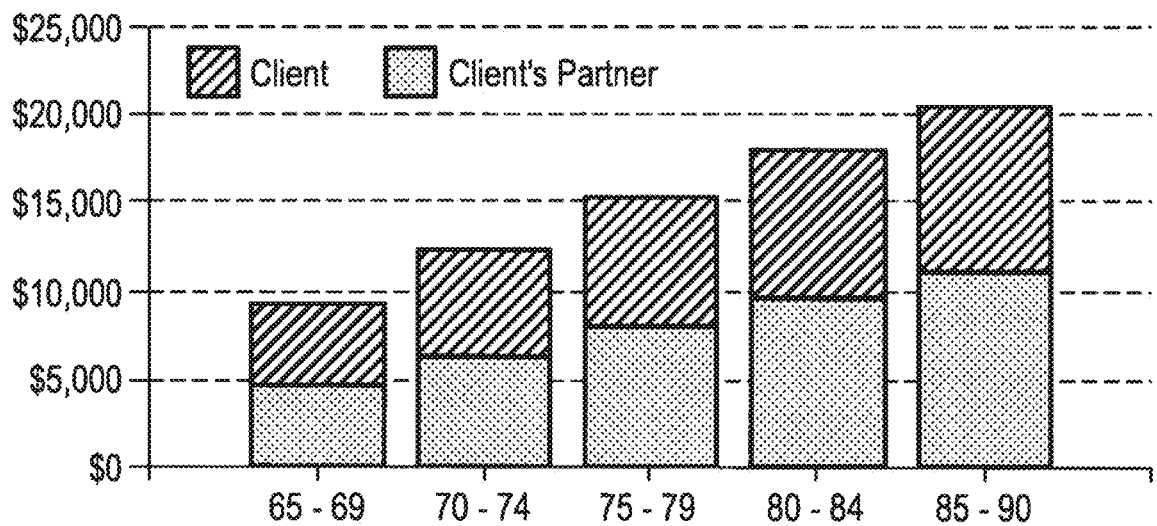
FIG. 7 is a bar chart showing estimated medical costs in retirement for both the client and the client's partner over five-year retirement periods.
Figure 9A:
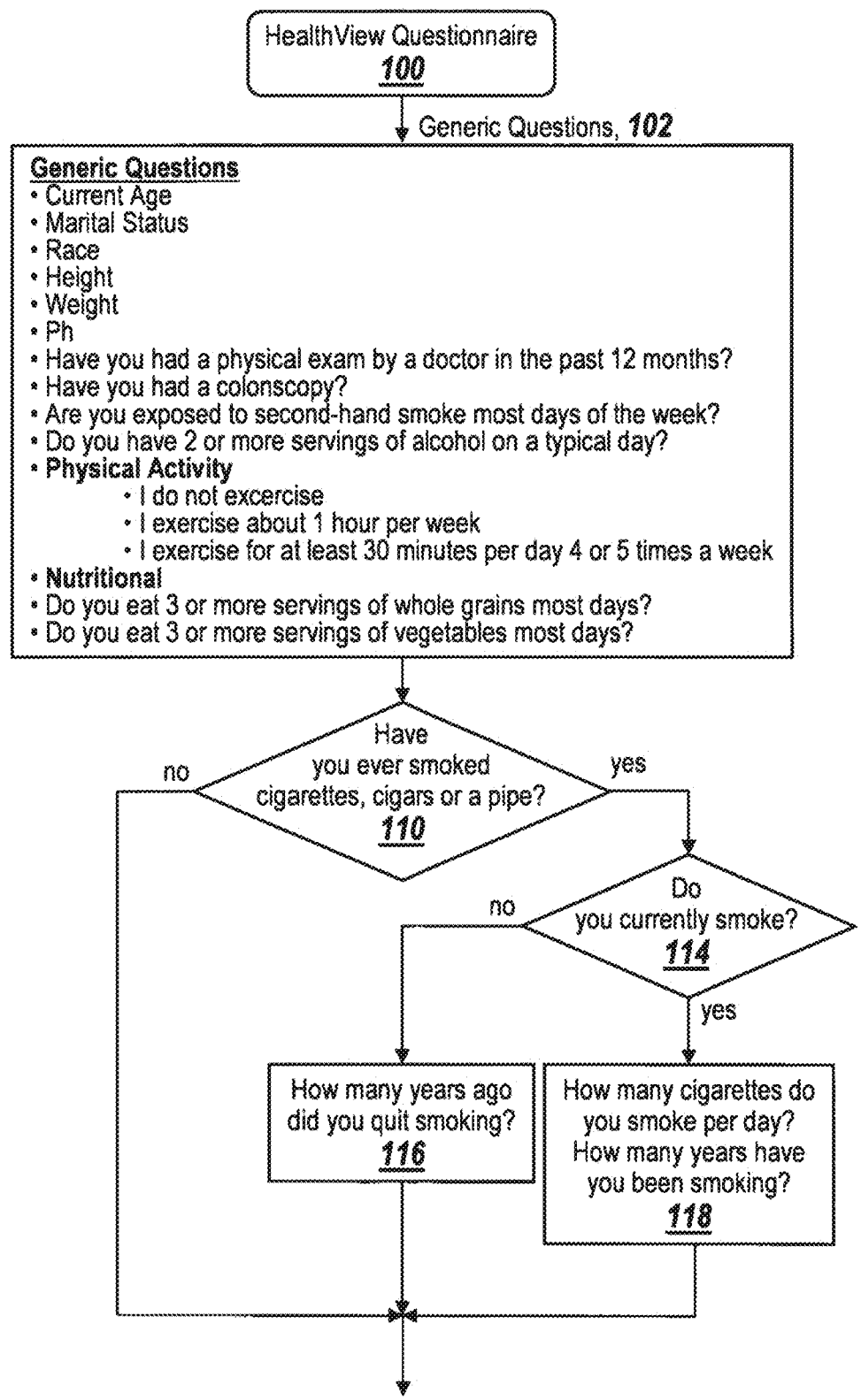
FIGS. 9A-9E are flow charts showing the operation of the subject system.
Figure 9B:
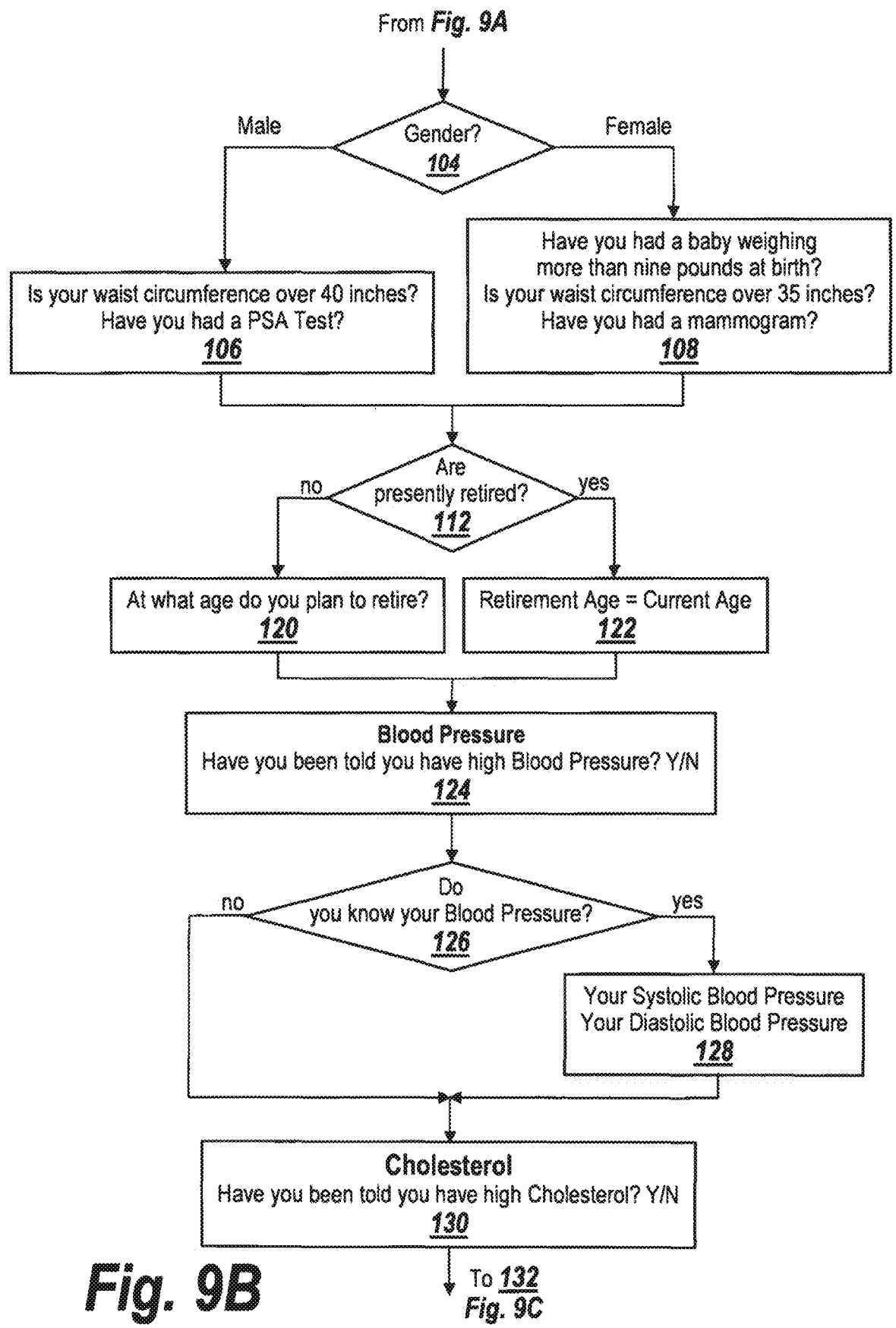
Figure 9C:
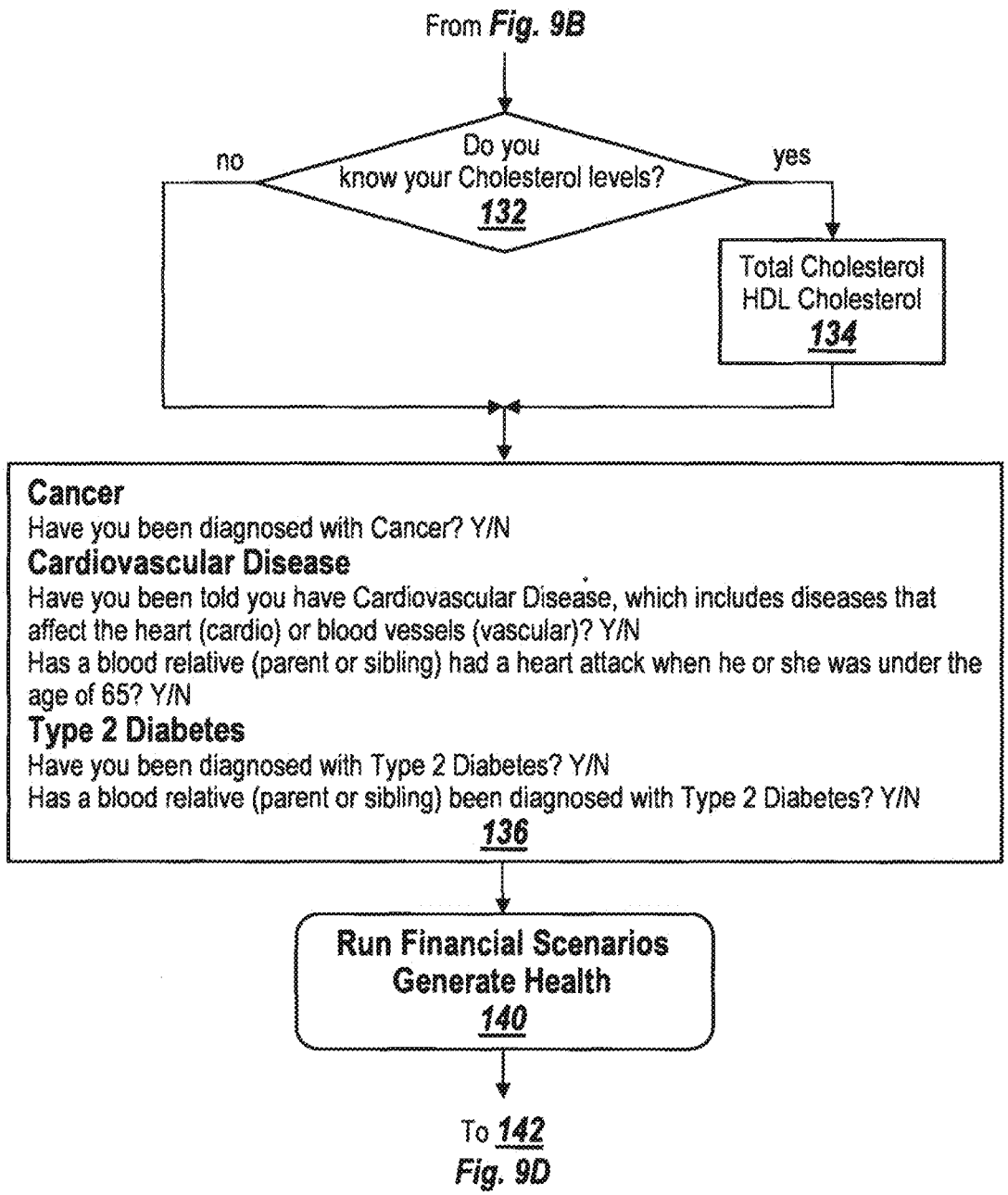
Figure 9D:
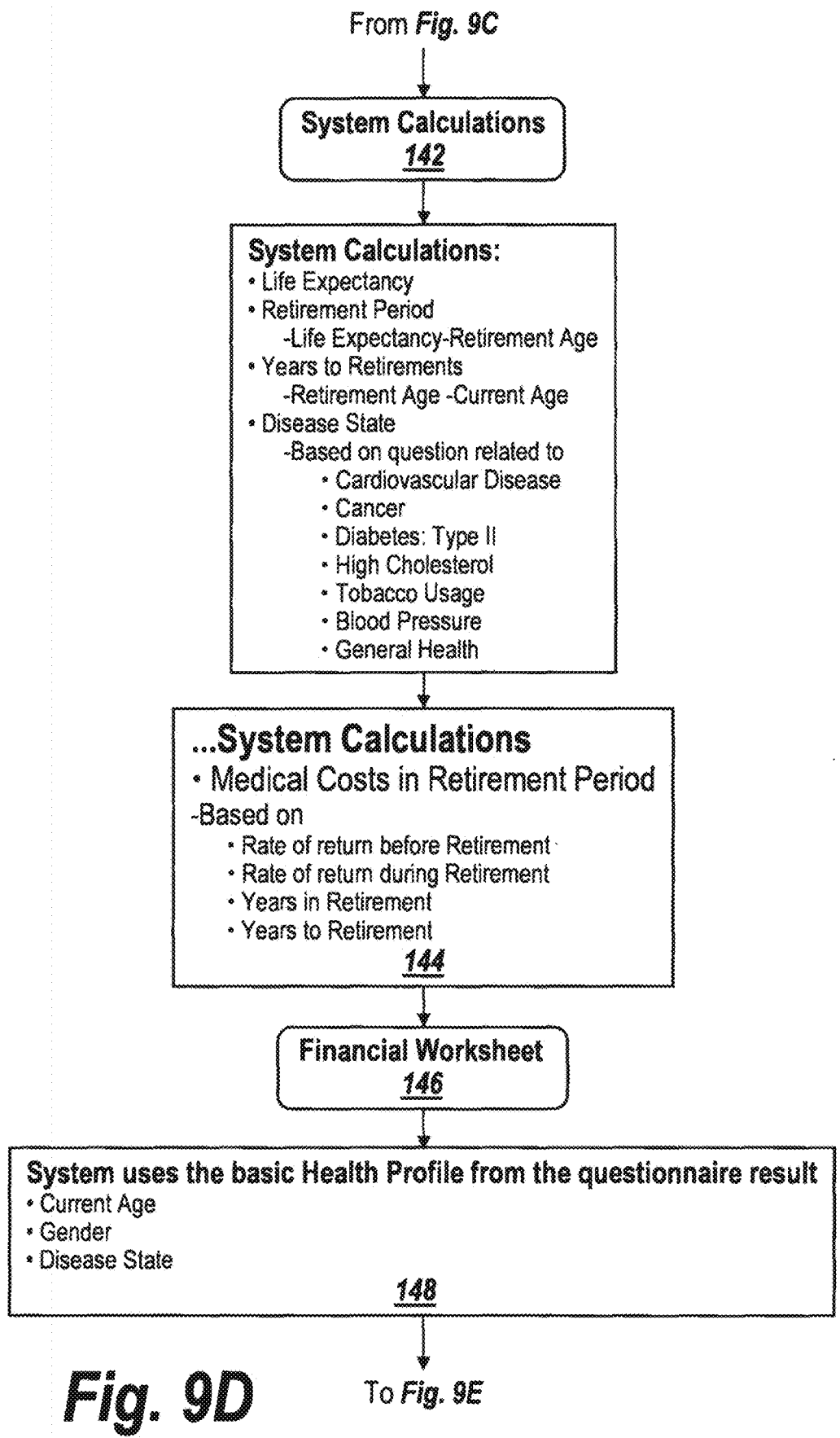
Figure 9E:
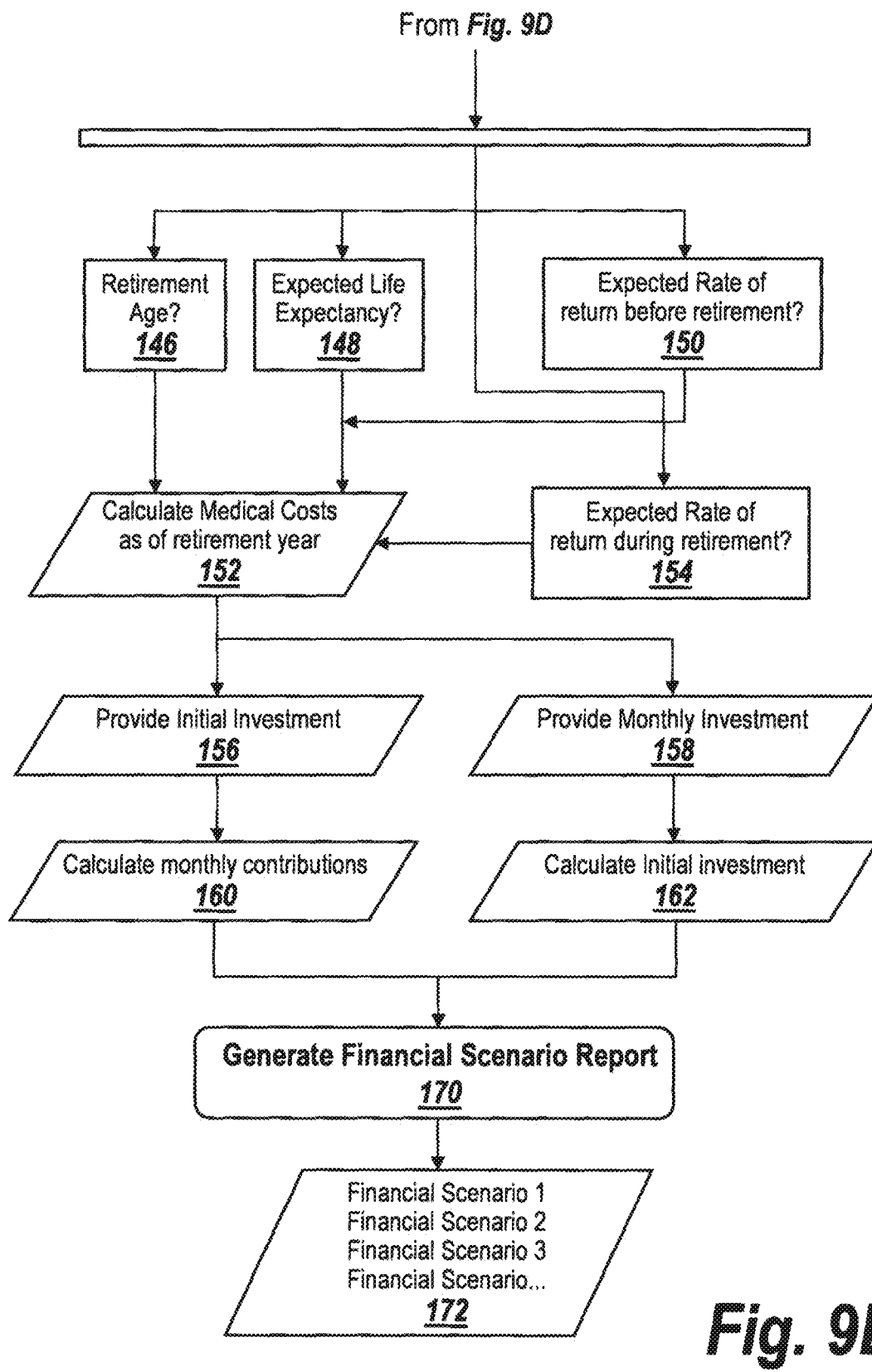

Referring to FIG. 7, one of the interesting outputs of the financial management tool is the ability to provide a visual output of the estimated medical costs in retirement over five year increments and to show the increase in estimated medical costs for either an individual or their partner. Here, the estimated medical costs in retirement can be computed on a five year interval based on a combined input from the client and the client's partner.

Referring now to FIG. 8, shown are two bar graphs that indicate the savings needed to cover medical expenses in retirement, for instance $216, 261 for an individual, versus the medical expenses in retirement, which are calculated to total $397, 587.

This indicates that early investing is needed to offset the total medical expenses in retirement, which typically exceed the savings necessary to cover these expenses.

In summary, what is provided by the financial management tool is an individualized report that calculates the necessary savings needed to cover medical expenses during one's retirement years. Since these medical expenses are the most significant expense during retirement, providing an individual with a calculation of the savings can assist in determining when to retire and the amount of assets or savings required to cover their health care expenses.

What follows are examples of how an individual can benefit from the use of the subject financial management tool.

Example I

As mentioned above, the primary use of the financial management tool is to determine how much money one will need to have saved at the point of retirement. Based on the retirement date and the expected return on savings and retirement, the financial management tool calculates how much savings must be accumulated in order to cover annual medical expenses.

For instance, a particular individual may need $120,000 in savings to cover $120,000 in health care expense. Note that the health care expense increases at about 5% annually. Assuming $120,000 in savings is required at the point of retirement, the system can calculate from today's date until the retirement date what one would need to save. For instance, one would need $38,000 in the present in order to have $120,000 at the point of retirement to cover the medical expenses.

Since medical expenses are the largest expense during retirement, it is not an expense that can be diminished by living in a smaller house or buying a less expensive car. One does not have these options with health care. Thus, the numbers that are going to have to be addressed are the actual projections based on the individual's health and status.

Example II

Another feature as mentioned before is that if a person needs $38,000 in savings today in order to have access to $120,000 at retirement, the financial management tool will inform the individual that if they have only $20,000 today, the subject tool will suggest they add an additional $32 per month to savings to reach their goal.

Example III

As noted above, one can choose rates of return and can run "what if" scenarios. For instance, the system can reflect the various financial implications of retiring at 65 years of age or at 67 years of age. The tool can be adjusted to various retirement dates and also on different rates of return during retirement.

If, for instance, one is involved in a growth portfolio on a compounded basis, the individual may be looking at 7% growth. However, during retirement assuming the portfolio is more conservative and goes to purchasing of treasuries, perhaps a 4% rate of return is a more reasonable rate. Thus, the individual an choose their potential rates of return and see what happens to the numbers.

Example IV

As mentioned before, retirees can use the financial management tool to calculate the cost going forward into retirement. One of the critical elements is determining an individual's life span. This becomes problematic with age. A healthy 40 year old has a very specific life span whereas a healthy 68 year old's life span will be significantly longer than a healthy 40 year old, the extent to which is difficult to judge. Thus, a person that is 68 would need to know their likelihood of living past 80 or 90 and what their health care expenses will look like.

Example V

Retirees generally operate on a budget and must know what impact their medical cost will have on their budget. Once this calculation is performed the question then becomes how long their money will last.

For instance, if the individual is spending between $3,000 and $4,000 a year on vacations that they were hoping to do on an annual basis until they are 75, they may be persuaded by the subject calculations to alter their spending habits. In order to inform the individual, one first has to calculate their health care expenses. Then, one has to provide a budget in today's dollars.

For instance if the budget is $30,000 a year for medical expenses, by the end of a 15 year period in which a 3% inflation rate is constant, medical expenses may be over $60,000 a year. It is important for individuals to know these numbers when establishing their budget and the subject tool in determining these adjusted costs. The next budget step is income sources. Assuming that a person has a $500,000 in savings, is going to generate $24,000 out of social security, has a small pension, and could potentially sell his or her house, the subject tool can calculate a distribution analysis on a year by year basis to show how the person's assets are dwindling and when they will run out. If one anticipates that they will live in retirement for 30 years, one could be out of money in 20 years. Thus creating a budget that takes into account the health care costs is an exceedingly useful function for the subject tool.

Example VI

As mentioned above, firms with over 100,000 employees are self-insured. The question of raises for employees presents certain problems. For instance, one needs to know whether to give an employee a 5% raise and how much the raise is really worth. With the financial management tool the company can quickly plug in a 7% increase in health costs so that in this scenario the employee is being given a 12% raise.

Example VII

The financial management tool provides realistic numbers based on a person's health history and other actuarial characteristics and provides disease management and wellness advice. As mentioned above, if an employee can better manage their health care, then cost savings can be significantly augmented. For instance, if an individual knows his age and health status, the financial management tool can output the life span of the individual. It is then possible to calculate the annual cost of health care because the company knows what portion the individual pays for and what portion the company covers. For example, if the individual does not follow a doctor's prescribed plan, instead of living to 78, the life span could be 67. There are associated annual costs for health care for the individual between the present time and age 67 which, for instance, may be different than the annual cost between the present time and 78. With successful coaching, information can be provided to the employee as an incentive to take the right action.

For instance, if the individual has type 2 diabetes and does not take care of his condition, he may die by the time he is 67 years old. If he takes care of himself properly, he may live to 78. Calculations from the calculator may indicate that he will be spending $800 a year if he takes care of himself, whereas he may be spending $1,400 if he does not take care of his condition.

What is now presented are a series of flow charts to indicate how the subject calculator operates.

Referring now to FIGS. 9A-9E, the process used by the financial management tool starts with a questionnaire 100 which poses generic questions 102, for example, questions such as current age, marital status, race, height, weight, date of last physical exam, date of last colonoscopy, exposure level to second-hand smoke, number of servings of alcohol in a typical day, level of physical activity, eating habits, etc. The output of the generic questions may be applied to a decision block 104 which takes the individual's gender into account. If male, questions such as illustrated at 106 ("is your waist circumference over 40 inches?", or "have you had a PSA test?") may be asked. If female, questions such as "have you had a baby weighing more than 9 pounds at birth?", "is your waist circumference over 35 inches?" and "have you had a mammogram?" may be asked at 108.

The results are passed to a decision block 110 which poses the question "have you ever smoked cigars, cigarettes or a pipe?" If the answer is no, then the workflow may proceed to decision block 112. If the answer is yes then as shown at decision block 114, the question is posed "do you currently smoke?" If the answer is no, the question is asked as illustrated at 116 "how many years ago did you quit smoking?" If the answer is yes, the question posed at 118 is "how many cigarettes do you smoke per day and how many years have you been smoking?"

The results of the outputs of blocks 116 and 118 are also applied to decision block 112 which asks the question "are you presently retired?" If the answer is no, then as illustrated at 120 a query is asked as to "what age do you plan to retire?" If yes, then the retirement age is set to one's current age as illustrated at 122.

The results are passed to block 124, which poses the question "have you been told that you have high blood pressure?" If yes, then as illustrated by block 126 the question is posed "do you know your blood pressure?" If yes, the question is posed at 128 to provide your systolic blood pressure and your diastolic blood pressure.

The outputs of these blocks are passed to a block 130 to ascertain "have you been told that you have high cholesterol?". The result is passed to decision block 132 which asks the question "do you know your cholesterol levels?" If yes, the person is asked at 134 to provide their total cholesterol and HDL cholesterol level.

The outputs of these blocks are both sent to block 136 which asks the questions relating to disease, namely "have you been diagnosed with cancer?", "do you have cardiovascular disease?", "have you been told that you have cardiovascular disease which includes diseases that affect the heart (cardio) or blood vessels (vascular)?" Also a question is posed "has a blood relative either parent or sibling had a heart attack when he or she was under the age of 65?" Again an answer yes or no is recorded. Finally the question is asked "have you been diagnosed with type 2 diabetes?", or "do you have a blood relative, parent or sibling that has been diagnosed with type 2 diabetes? The results are passed to a module 140 that runs financial scenarios which employs a plurality of system calculations 142. These calculations 142 may include, for example, life expectancy, retirement period in terms of life expectancy minus retirement age, years to retirement, i.e. retirement age minus current age, disease state based on questions relating to cardiovascular disease, cancer, type 2 diabetes, high cholesterol, tobacco usage, blood pressure and general health. The system calculations, as illustrated at 144, result in a calculation of medical costs in the retirement period based on the rate of return before retirement, the rate of return during retirement, years to retirement, and years in retirement.

The output of the system calculations 144 is reflected in a financial worksheet 146 in which the system uses the basic health profile from the questionnaire to indicate current age, gender and disease state.

From this financial worksheet 146, one ascertains retirement age 146, expected life expectancy 148, and the expected rate of return before retirement 150, the outputs of which are referred to a calculator that calculates medical costs 152, which in turn is reflected in the expected rate of return during retirement as illustrated at 154. The calculated medical costs are then inputted to a module that, calculates monthly investment 158, monthly contributions 160 and the initial investment 162. Finally, at 172 a financial scenario report 170 is output which provides a number of different financial scenarios based on a number of different variables.

Calculating Healthcare Expense

After the questionnaire is completed, the system determines health status and calculates life expectancy based on Current Age, Gender and Disease state. The information is saved in a database and used in calculating detailed healthcare costs.

The financial management tool utilizes stored procedures to calculate the medical costs that are required in retirement from actuary tables.

The stored procedure Input parameters are:
Client
    Current Age
    Gender
    Disease State
    Expected Life Expectancy
    Retirement Age
Spouse (if spouse information collected)
    Current Age
    Gender
    Disease State
    Expected Life Expectancy
    Retirement Age
Rate of Return before Retirement
Rate of Return during Retirement
Flag to determine if calculation should be at Net Present Value or at Present Value as of Retirement Year The stored procedure returns a data set that is comprised of multiple data tables. These data tables are used to populate graphs, charts and grids on the reports and forms.

Processing Steps

The stored procedure performs the following steps:

Get information from Actuary tables to a local data table based on input parameters from retirement age to 100 for client and spouse; the data table being populated with:
    ItemRetId
    ClientID—Client or spouse
    DiseaseState
    Gender—M/F
    Current Age
    Calculated Year
    LifeExpectancy
    AttainedAge
    Total out-of-pocket expenses
    Hearing
    Vision
    Premiums
    Dental
    TotalCost
    Adjusted out-of-pocket expenses
    Adjusted Premiums
    Adjusted Dental
    Adjusted Total Cost
    Healthcare Cost in Retirement
    HealthcareCost During Retirement
    Set ItemRetId as a Difference Between Attained Age and Retirement Age Calculate adjusted costs to Present Value as of Retirement year for client and spouse using:
    HealthcareCostinRetirement
    AdjustedPremuims
    AdjustedDental
    AdjustedTotalCost Calculate total costs as of Retirement year for client and spouse based on the retirement period (retirement age to expected Life expectancy).

Calculate time to horizon (Retirement age-current age) and calculate investment Required at Net Present Value.

Determine the joint retirement period, lowest retirement age to largest life expectancy and determine the three cut-off groups based on the earliest retirement of the two and oldest life expectancy using data related to:
    Client
    Spouse and Client Spouse
Or:
Spouse
Spouse and Client
Client
Calculate Total Costs for Client and Spouse in Retirement Periods
Create output data table that includes annual costs for premiums, out-of-pocket expenses, dental, hearing, vision and total costs for client, spouse and both. Create output data table that includes annual costs and average costs at a selected interval during retirement period (default every 5 years) for client, spouse and both. The table includes premiums, dental and out-of-pocket expenses, hearing and vision. Create output data table for client and spouse that displays
Retirement category
Retirement
at retirement year
during retirement
Initial investment
Period—number of years
Slope (%)

The information from the tables provides estimated projected costs closest to actuary tables for graphs and planning tools. Create an output table with all data collected and processed from the current age to 100 to allow use of the raw data in calculating what if scenarios, and to update grids, charts and graphs. Create a summary output table of cost required for client and spouse.

Actual Claims, Actual Cost Database

As stated hereinbefore, it has been found that the accuracy of the financial predictions of the subject financial management tool can be immeasurably improved by using actual claims data and actual cost data for these claims.

Figure 10:
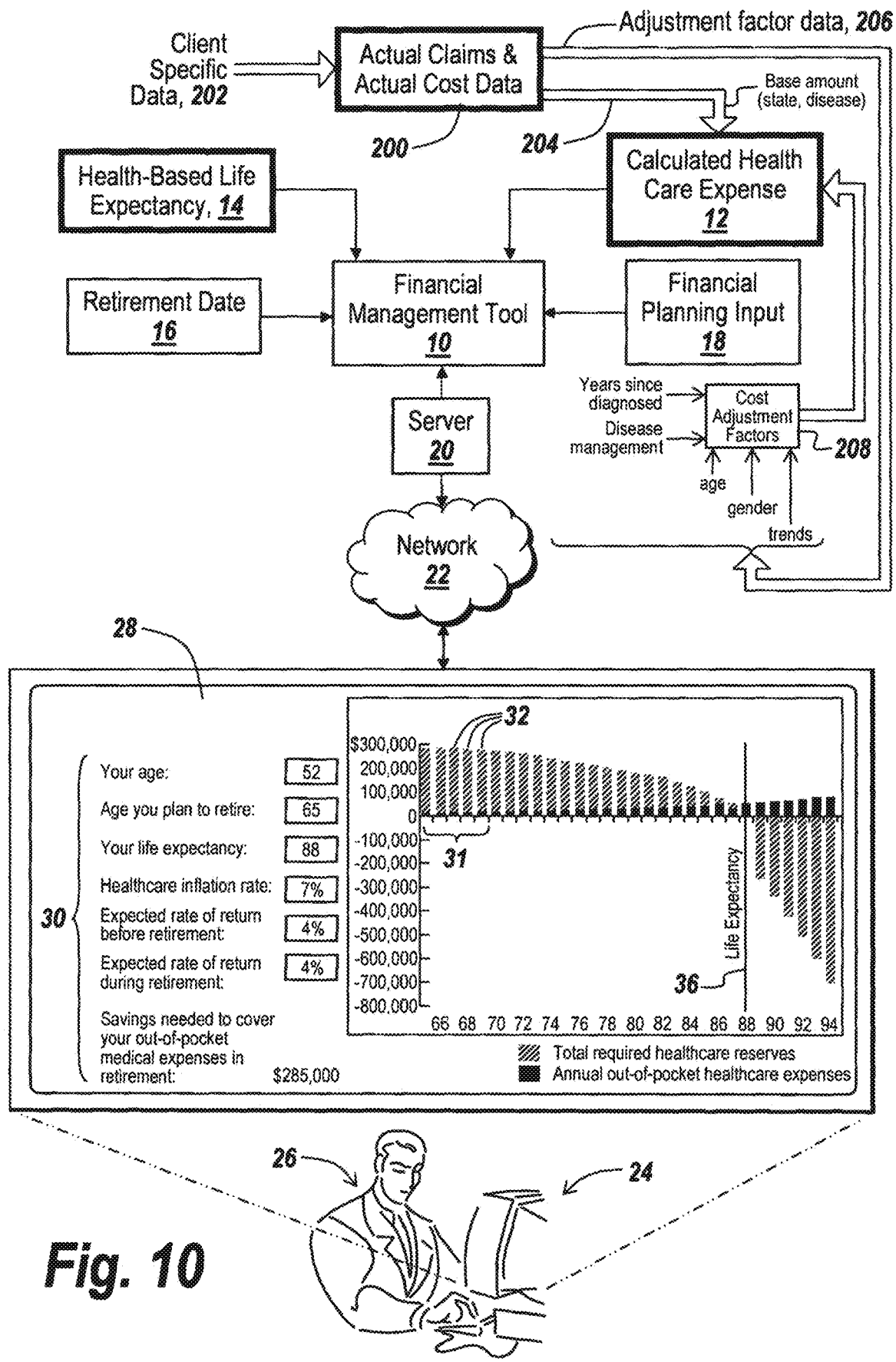
FIG. 10 is a diagrammatic representation of the use of actual claims and actual associated costs in providing precise actuarial data to the covered healthcare expense module of FIG. 1.

Referring now to FIG. 10, the financial tool of FIG. 1 is replicated with items carrying like reference characters.

Added as an overlay to the system of FIG. 1, as shown in FIG. 10, an actual claims and actual costs database 200 is utilized to develop a base amount for a given illness or disease based on the state of retirement for the particular individual as input in terms of client specific data 202. This base amount 204 is coupled to the calculated healthcare expense module 12, along with adjustment factor data 206 from database 200. This adjusted factor data 206 is applied to a cost adjustment factor module 208 which in one embodiment adjusts the base amount output from database 200 by, for example, the number of years since the disease was diagnosed, the disease management regime, the age, and the gender of the client as well as certain trends. These factors are used as adjustment factors to the base amount from database 200.

Figure 11:
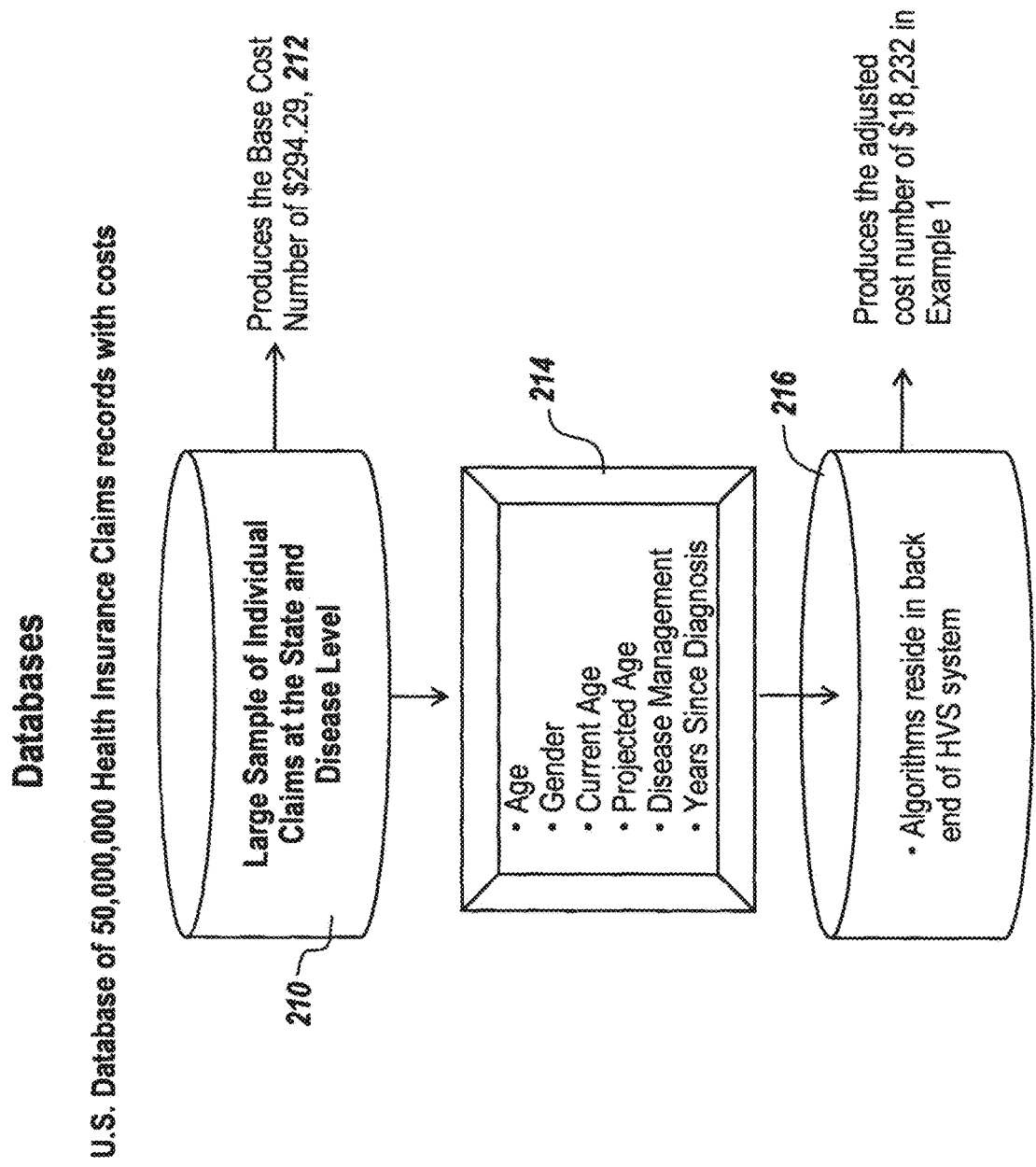
FIG. 11 is a flow chart of the actual claims and actual cost database of FIG. 10 showing the generation of a base healthcare cost number and the cost adjustment due to an individual's profile.

Referring now to FIG. 11, the databases utilized in the subject invention include for instance, a U.S. database of over 50 million health insurance claims records and costs. This large sample, illustrated at 210, is a large sample of individual claims arranged according to state and disease level which for instance produces a base cost 212, such as $294.29. the database is also queried as to the individual profile entered into the front end of the system which determines which factors need to be adjusted from the base cost.

In one embodiment, these items involve an adjustment factor for age, gender, current age, projected age, disease management regime, and years since diagnosis. These items are then provided as inputs to algorithms that reside in the subject system, namely algorithms 216, which produce, in one embodiment, an adjusted cost for hospital care in the amount of $18,232.00 in an example to be described in reference to FIG. 12. Note that the individual profile 214 is stored in cost adjustment module 208 of FIG. 10 and includes for instance, how the disease is managed, costs in the last two years of life, long term costs, annual updates to projections based on cost trends, regular updates from the Affordable Care Act and other factors. It is these factors which drive algorithms 216, such that given a base cost of $294.29, the adjusted cost number in one example of a poorly managed health regime is $18,232.00.

How these adjustments are applied is shown in the table of FIG. 12. Here the information is for a 45 year old male in Alabama with poorly managed diabetes. The information in the table of FIG. 12 shows how the base cost estimate of $294.29 is adjusted for the profile of the individual for a 21 year projection to 2033, age, gender, disease management and years since diagnosis to produce a total out-of-pocket hospital cost of $18,232.43 in 2033.

It will be seen that the $18,232.43 cost relates to the hospital costs for an individual age 65 in the year 2033 which is derived as follows. The base amount for the hypothetical 45 year old male is $294.29 based on a diabetes type II managed poorly scenario. This cost is derived from database 200 and utilizes actual claims and actual cost data.

It is noted that, in this case, the disease was diagnosed less than a year ago. This number is trended forward 21 years at a rate of 7% to yield a cost of $1,218.52. Thereafter, one applies age/gender factor of 971.610% to yield a hospital cost of $11,839.24. Following this is applied a disease management factor for the poorly managed scenario noted of 154.000% which yields a hospital cost of $18,232.43. It is noted that this is one of the costs associated with healthcare in a person's retirement based on a 21-year projection.

From what has been presented, the creation of adjustment factors for the base cost involves a full set of base cost data tables and adjustment factors created for each of the cost items shown across the top of the table in Example 1, namely medical premium individual, Rx premium individual, medical premium employee base, Rx premium employee base, dental premium, hospital out-of-pocked (OOP) costs, doctor and tests OOP costs, Rx OOP costs, dental OOP costs, hearing OOP costs, vision OOP costs and using the actual claims data records and costs available in database 200.

As to the base cost data the table shown below is only for hospital OOP costs. The base data for the hospital OOP costs are taken directly from the claims database for each state and chronic disease condition. These costs are shown below:

TABLE 1

| | Costs for 2013 | | |
|---|---|---|---|
| State | High Blood Pressure | High Cholesterol | Diabetes |
| AL | $200.44 | $144.03 | $294.29 |
| AK | $340.25 | $244.60 | $499.68 |
| AZ | $232.80 | $167.44 | $342.04 |
| AR | $167.16 | $120.26 | $245.59 |

In one embodiment, rather than creating a similar table for every possible characteristic or combination of characteristics in a patient's profile, such as current age, gender, life expectancy and income and for every possible year that the individual ages into through retirement, the database creates a set of adjustment factors. This constitutes a thinner set of adjustment factor formulas which allows the subject system to contain significant less raw data and thus decrease the time in which a cost estimate can be produced.

Once an individual's profile information has been input, the adjustment factors are applied to the base cost data to appropriately reflect correct costs for that particular individual.

It is noted that the adjustment factors are also derived directly from the claims database and are stored as a separate file. Every time the system is updated with any particular type of legislative, cost trend or other changes, both the database table files and the adjustment factor files are imported into the subject system.

The adjustment factor file is created from the original claims data file as follows.

First, a statistical software program such as SAS or SPSS is run on the claims database. This program compares the cost data in each of the columns of actual cost data as illustrated below and creates an adjustment factor. This can be seen below.

TABLE 2

Actual Hospital OOP Costs From Claims Data for Each Defined Group of Claimants

| State | Diabetes Cost 2013 (Base Costs) | Diabetes Cost Increase over Base (5 yrs. - 2018) | Diabetes Cost For Male 65 yrs. old (2018) | Well-managed Diabetes Cost For Male 65 yrs. old (2018 | Poorly-managed Diabetes Cost For Male 65 yrs. old (2018 |
|---|---|---|---|---|---|
| AL | $294.29 | $1218.52 | $11,839.24 | $ 8879.43 | $18,232.40 |
| AK | $446.68 | $2068.98 | $20,102.38 | $15,076.79 | $30,967.37 |
| AZ | $342.04 | $1416.25 | $13,760.44 | $10,320.33 | $21,131.08 |
| AR | $245.59 | $1016.90 | $ 9,880.29 | $ 7,410.22 | $15,512.65 |

The data in these columns can be used to predict future costs from predictive or prognostication algorithms that take the actual historical base cost data and compare it to, for example, the prior 10-year history of cost increases to accurately predict trends.

Adjustment Factors

| State | Diabetes Cost 2013 (Base Costs) | Diabetes Cost Increase over Base (5 yrs. - 2018) | Diabetes Cost For Male 65 yrs. old (2018) | Well-managed Diabetes Cost For Male 65 yrs. old (2018 | Poorly-managed Diabetes Cost For Male 65 yrs. old (2018 |
|---|---|---|---|---|---|
| AL | $294.29 | 414.06% | 971.61% | 75.0% | 154.0% |
| AK | $446.68 | 414.06% | 971.61% | 75.0% | 154.0% |
| AZ | $342.04 | 414.06% | 971.61% | 75.0% | 154.0% |
| AR | $245.59 | 414.06% | 971.61% | 75.0% | 154.0% |

Next, using a statistical methodology known as analysis of variance (ANOVA), the adjustment factors may be tested for statistical accuracy and reliability. This test typically requires a very large number of claims in each of the above columns, such as, a minimum of 2,000 claims, in order to be statistically reliable. Only adjustment factors which are statistically reliable may be saved in the cost adjustment factor module 208.

The actual claims data and actual costs of resolving the actual claims may be used both for the base number for a particular state and disease, and to formulate the adjustment factors which are used to adjust the base cost. As a result, a financial management tool that utilizes both the actual claims and actual costs involved to resolve the claims results in a highly sophisticated extremely accurate predictor of healthcare costs in the retirement of the client.

Reference will now be made to FIGS. 13-19, which show various non-limiting examples of a user interface, in accordance with an embodiment. Thus, it should be understood that the following are solely for illustrative purposes and are non-limiting in scope.

FIG. 13 depicts an example embodiment of a user dashboard 1300. As discussed herein, a user may have an individual authentication method to allow them to create, access, update, and/or delete various personal information from the system. Accordingly, the dashboard provides various navigation tools in the menu 1301. In some embodiments, and as shown, the system may provide one or more links in the menu 1301 to access various features of the system (e.g., a user's current healthcare projections, a questionnaire to generate their health profile, personalized health tips through the health coach, graphs showing the user's health progress over time relating to site-generated, input data from wearables, and user input data, etc.).

In another embodiment, important information for the user to track may be displayed directly on the dashboard with options for user input where applicable. This information may include, as shown, current life expectancy estimates 1302, weight 1303, hemoglobin A1C test levels for diabetics 1304, and financial snapshots 1305. In a further embodiment, the user may also be presented with some highlights from a health coach (e.g., a tip of the day 1306, recommended recipes 1307, recommended exercises 1308, etc.). Accordingly, the system may provide suggestions on a wide range of subjects including healthy eating, exercise, and finances.

According to an embodiment, a new user may first generate a health profile. Referring now to FIG. 14, a portion of an example questionnaire is shown 1400 to begin a profile. As shown, and further discussed herein, information captured may comprise date of birth 1401, gender 1402, race 1403, height 1404, and weight 1405. In a further embodiment, various other demographic information may be included in the questionnaire, such as, for example, marital status, education, employment, income (e.g., household or individual), living status (e.g., homeowner, renter, homeless, etc.), number of children/dependents, etc.

Figure 15:
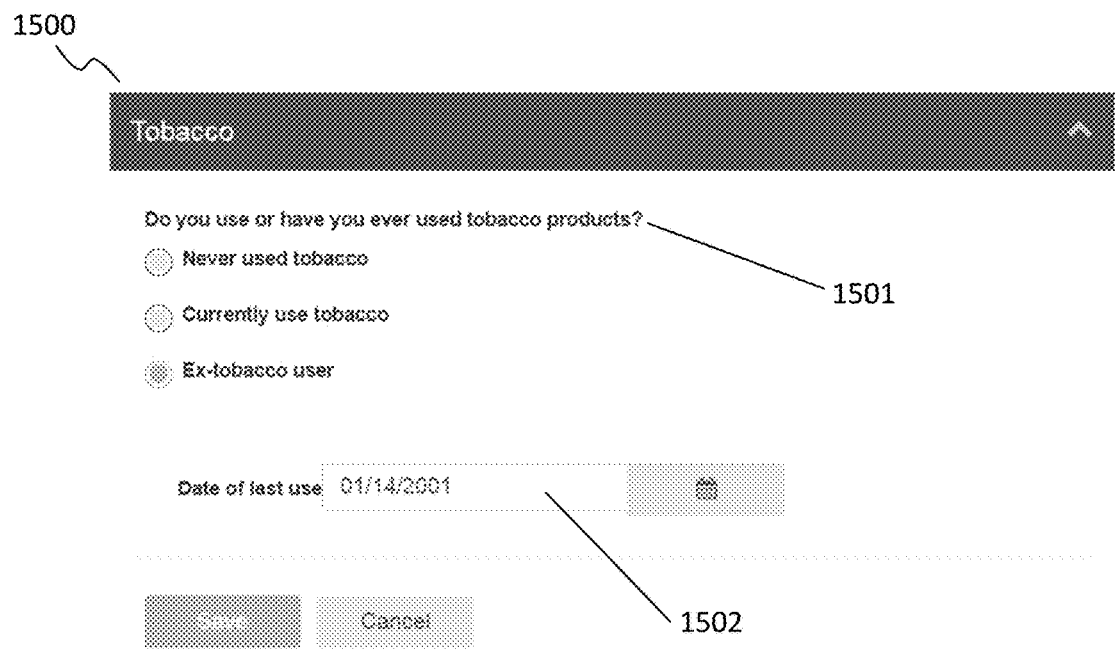
FIG. 15 depicts a tobacco usage questionnaire as part of a health profile in accordance with an embodiment.

FIG. 15 depicts another example embodiment, which requests tobacco usage information 1500. As discussed herein, one or more of the questionnaire forms may be dynamic in nature. Accordingly, as shown, if a user were to select "ex-tobacco user" 1501, the questionnaire user interface may automatically generate a new form 1502, which requests the date of last use. Similarly, if a user were to select "currently use tobacco" 1501, the system may, in one embodiment, request a date of first use and/or a usage quantity (e.g., half a pack a day, 2 packs a day, etc.). Accordingly, in some embodiments, the system may request various health related information, and modify and/or update the remaining questionnaire based on the input received.

A further example embodiment is shown in FIG. 16 that relates to a blood pressure questionnaire 1600 as part of an embodiment. As shown, the questionnaire may establish the user's 1601 and their family's 1602 medical history as it relates to high blood pressure. As discussed herein, the questionnaire may then require additional information based on the received response (e.g., current blood pressure 1604 if known 1603, current and historical blood pressure medications 1605, adherence to doctor's instruction 1606, alcohol usage 1607/1608, and diet (e.g., salt 1609, potassium 1610, vitamin D 1611, etc.).

Similarly, FIG. 17 depicts an example embodiment related to diabetes 1700. Although various questions are shown in FIG. 17, it should be understood that some embodiments may require more or fewer questions depending on the patient. For example, if a patient, and patient's family, has never been diagnosed or suffered from any form of diabetes, various questions would clearly be superfluous. Accordingly, in some embodiments, the system may prompt a user to indicate if they have been diagnosed with diabetes 1701, a diabetes type 1702, if insulin is used 1703, if an A1c value is known 1704, what the A1c value is 1705, if a fasting blood sugar value is known 1706, what the fasting blood sugar value is 1707, number of prescribed medications 1708, use of a diabetic diet 1709, attendance of doctor appointments 1710, and diabetes related family history 1711.

FIG. 18 depicts an example embodiment related to a cholesterol questionnaire 1800. According to some embodiments, and as shown, the system may further request information related to being diagnosed with high cholesterol 1801 and 1802, family history with heart disease 1803 and 1804, if current cholesterol is known 1805, and if so the values 1806, 1807, and 1808, current or historical medication 1809, waist size 1810, quantity and type of fats eaten 1811 and 1812. In some embodiments, additional information may be available to a user via information buttons 1813. If a user clicks on an information button, the system may, in some embodiments, provide the user with additional information relative the specific question referenced (e.g., via a pop up window, new tab, etc.).

FIG. 19 depicts an example embodiment related to a weight questionnaire 1900. According to some embodiments, and as shown, the system may request information related to highest adult weight 1901, age at highest weight 1902, family obesity 1903, exercise amount 1904, and eating habits 1905.

Health care projections, including life expectancy and cost, not only include the projection based on the user's current health and lifestyle, (e.g., lifestyle relates to whether a patient is not following protocols, following a limited number of protocols, or all protocols, based on morbidity or co-morbidity factors, diet, exercise, etc.) but may also include behavior modifications (e.g., better, best, etc.) and projected ramifications of said modifications. Accordingly, in an embodiment, projections may include current, better, and best modifications tailored to the user's health.

Accordingly as discussed herein, in some embodiments, a system may provide actuarial health care cost and longevity projections to one or more clients in the financial services industry, benefits consultants, wellness companies, and corporate plan sponsors. The data may be used to create customized cost projections, cost savings projections relative to alternative health scenarios, and longevity projections, manifested in any of the following methods: client-facing web applications, financial professional-facing web applications, APIs, or marketing content featuring hypothetical client info. As further discussed herein, and explained via various examples, the process involves in-taking variables (e.g., inputs) and developing projections (e.g., outputs) within the utilization of actuarial health data.

Figure 20:
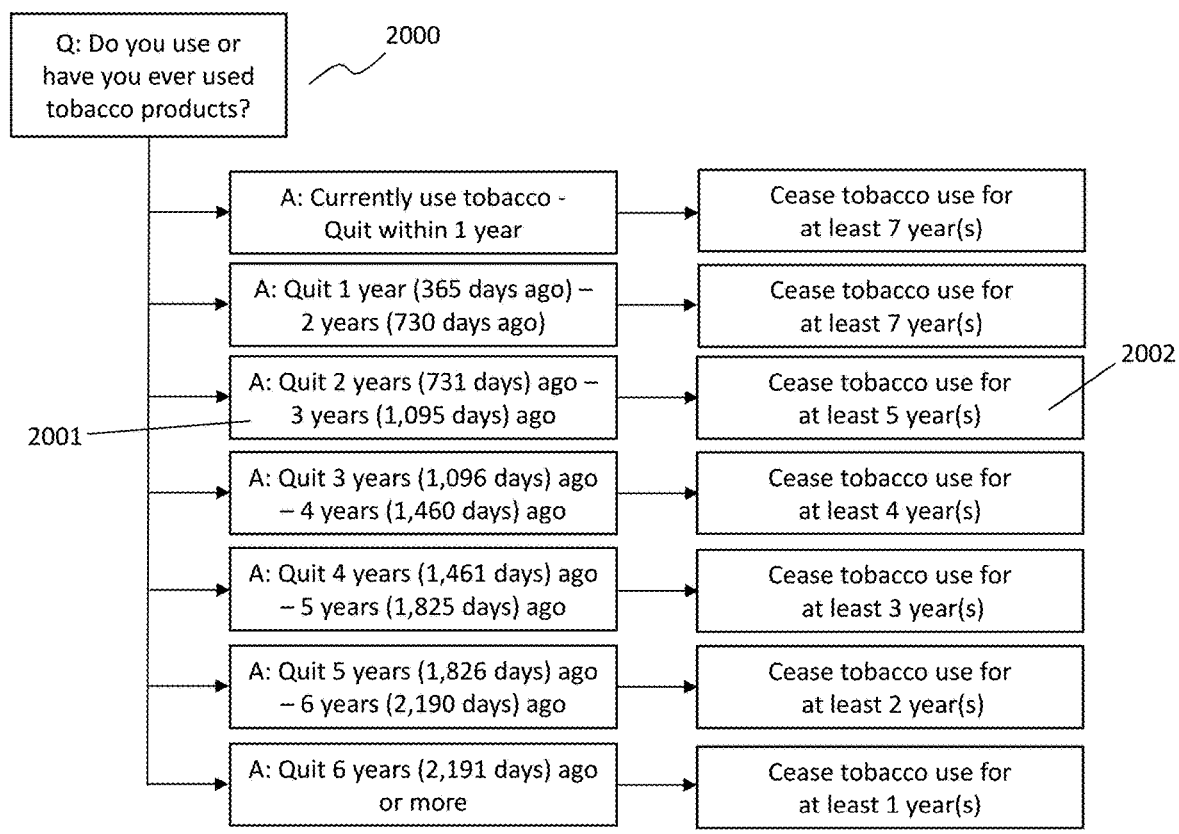
FIG. 20 depicts a flowchart of potential behavior modifications relating to tobacco usage based on user input in accordance with an embodiment.
Figure 21:
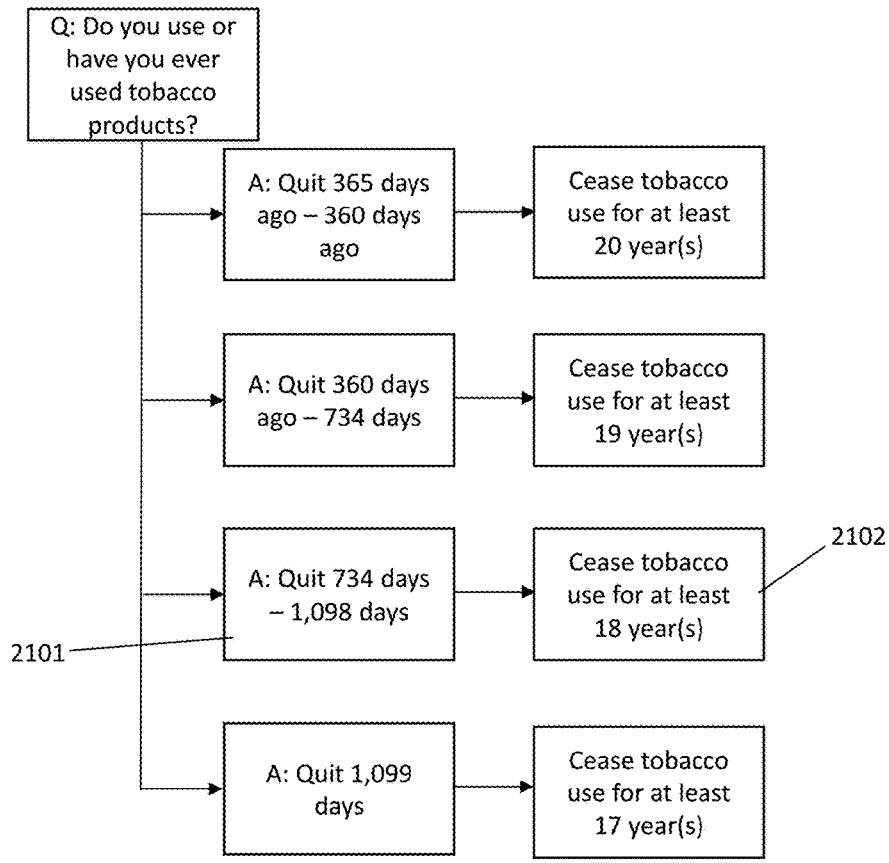
FIG. 21 depicts a continuation of the flowchart of potential behavior modifications relating to tobacco usage based on user input in accordance with an embodiment.

FIGS. 20 and 21 illustrate a flow chart 2000, in accordance with an embodiment, for determining better and best behavior modification scenarios in relation to tobacco usage. Accordingly, as shown, if a user is determined to be a current or historical tobacco user, the system can determine a better and/or best option based on the received input. For example, if a user is determined to have quit smoking between 2 and 3 years ago 2001, the system may generate a "better" option which indicates they need to continue to cease tobacco use for at least 5 more years 2002. In a further embodiment, the system may generate a "best" option 2100 that based on knowing the user quit smoking between 2 and 3 years ago 2101, may generate a "best" option indicating a need to continue to cease tobacco use for at least 18 more years 2102. In another embodiment, the system may set milestones for the user in terms of ceasing tobacco usage in both situations.

FIGS. 22 and 23 illustrate a flow chart, in accordance with an embodiment, for determining, respectively, the better and best behavior modifications for users with high blood pressure and/or hypertension. As shown, in some embodiments, suggested modifications may comprise limiting salts, taking medications as directed, continuing physical activity, increasing physical activity, drinking in moderation, etc.

FIGS. 24 and 25 illustrate a flow chart, in accordance with an embodiment, for determining, respectively, the better and best behavior modifications for users with diabetes. As shown, suggested modifications may comprise following a diabetic diet, properly monitoring your symptoms, attending regular checkups, taking medications as directed, continuing physical activity, increasing physical activity, etc.

FIGS. 26 and 27 illustrate a flow chart, in accordance with an embodiment, for determining, respectively, the better and best behavior modifications for users with high cholesterol. As shown, suggested modifications may comprise choosing healthy fats, taking medications as directed, limiting salt intake, and continuing physical activity, increasing physical activity, etc.

Figure 28:
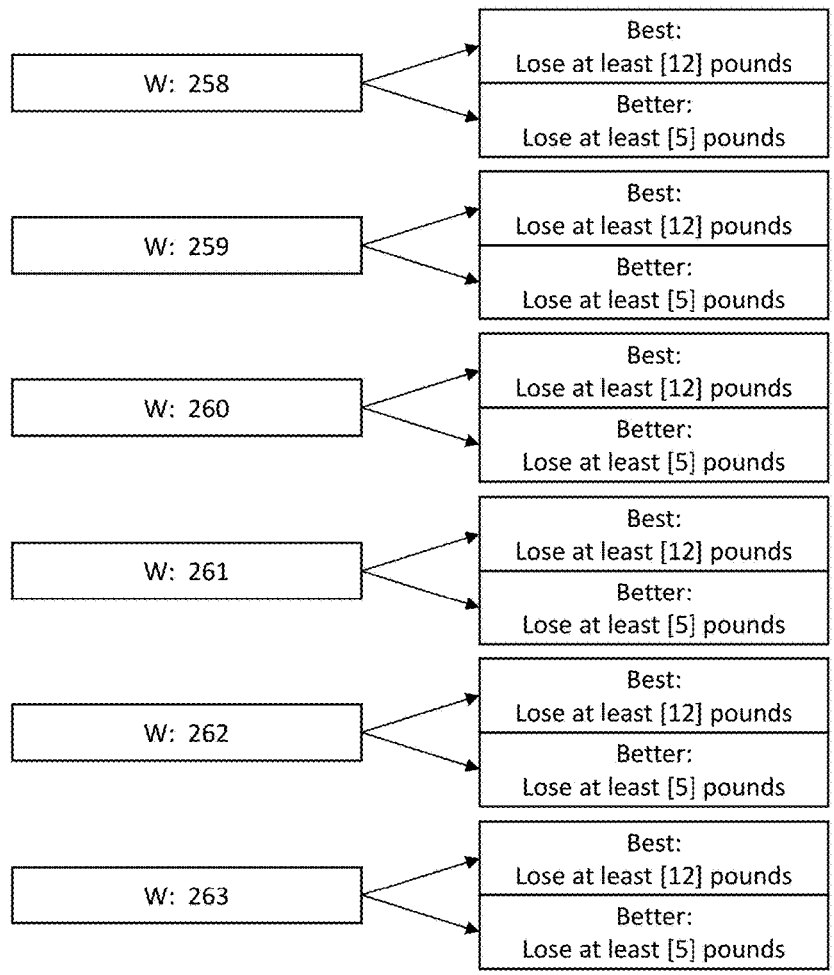
FIG. 28 depicts a flowchart of potential behavior modifications relating to weight based on user input in accordance with an embodiment.
Figure 29:
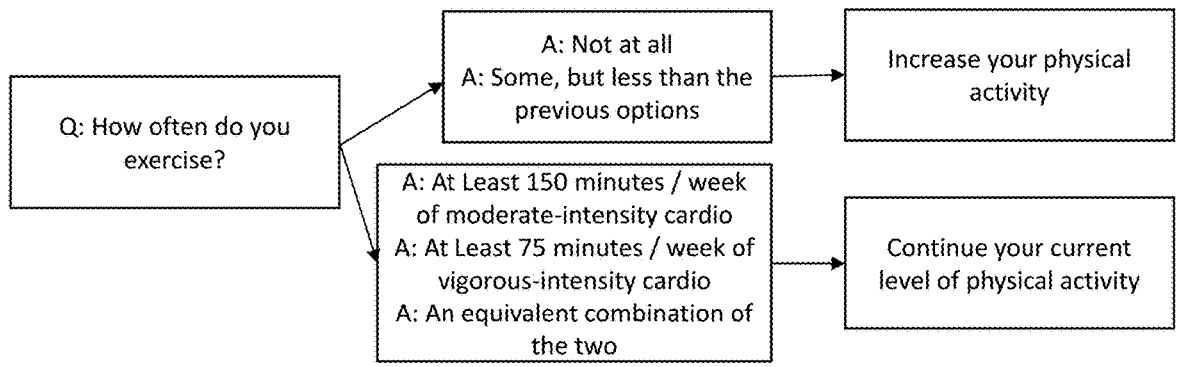
FIG. 29 depicts a continuation of the flowchart of potential behavior modifications relating to weight based on user input in accordance with an embodiment.

FIGS. 28 and 29 illustrate a flow chart, in accordance with an embodiment, for determining the better and best behavior modifications for overweight users. As shown, suggested modifications may comprise losing a specified amount of weight, continuing physical activity, increasing physical activity, etc. In one embodiment, the system may highlight financial and life expectancy modifications by only committing to adopting a limited number of changes in lifestyle, or a custom account of change. For example, the system may generate results based on claims data for losing as little as two pounds.

Figure 30:
FIG. 30 depicts health and healthcare cost projections based on current health and potential behavior modifications in accordance with an embodiment.

Referring now to FIG. 30 a illustrative embodiment of a user interface 3000 is shown displaying projections of the user's life expectancy 3001, healthcare costs 3002, added disposable income 3003, and savings value 3004. As discussed herein, these values may be calculated based on all, or a portion, of a user's input regarding their lifestyle, demographic data, existing claims data, and custom algorithmic based factors. In addition to the calculated values, the system may, in some embodiments, provide an "action plan" 3005 which may lay out various suggestions and/or comments regarding a user's lifestyle and what changes may lead to increased life expectancy and/or reduced costs (e.g., a 'better" 3006 or "best" 3007 plan).

Accordingly, the determined values (e.g., 3001, 3002, 3003, and 3004) may be adjusted according to a user's indication that they will follow one or more of the suggested behavior modifications discussed in the action plan 3005 that may be divided into "better" 3006 and "best" 3007.

Figure 31:
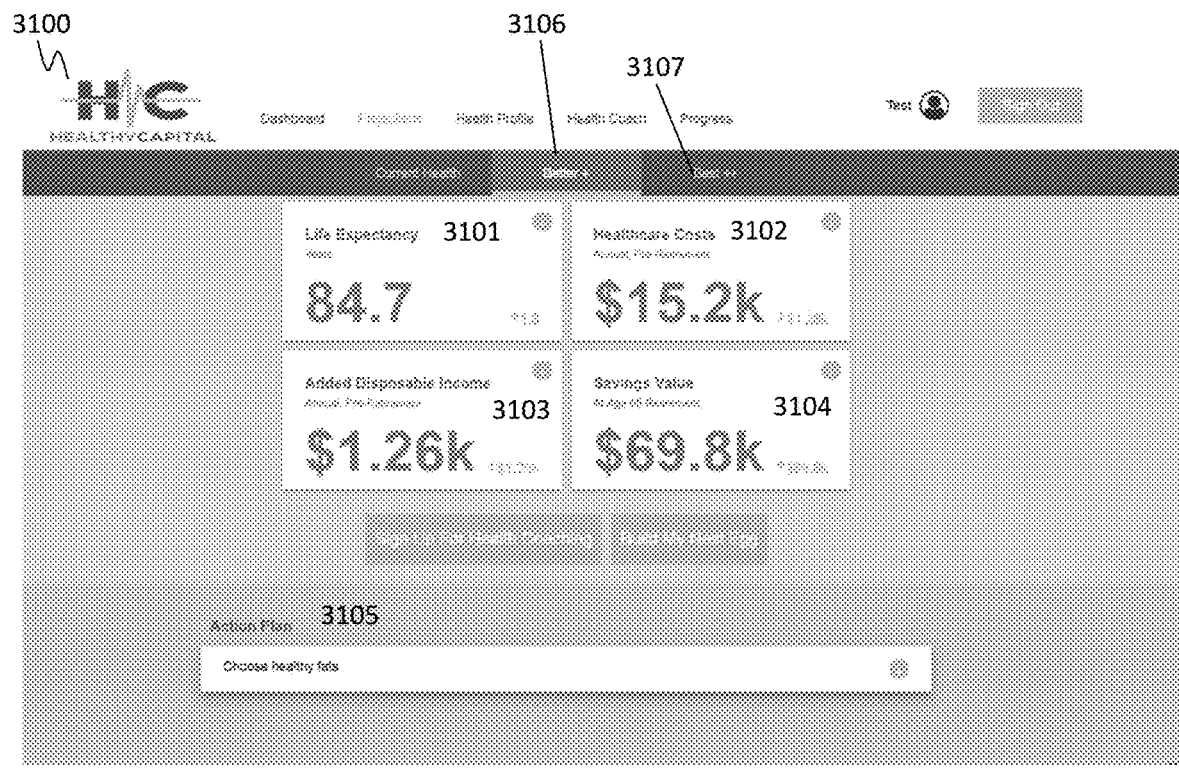
FIG. 31 depicts health and healthcare cost projections based on better potential behavior modifications in accordance with an embodiment.
Figure 32:
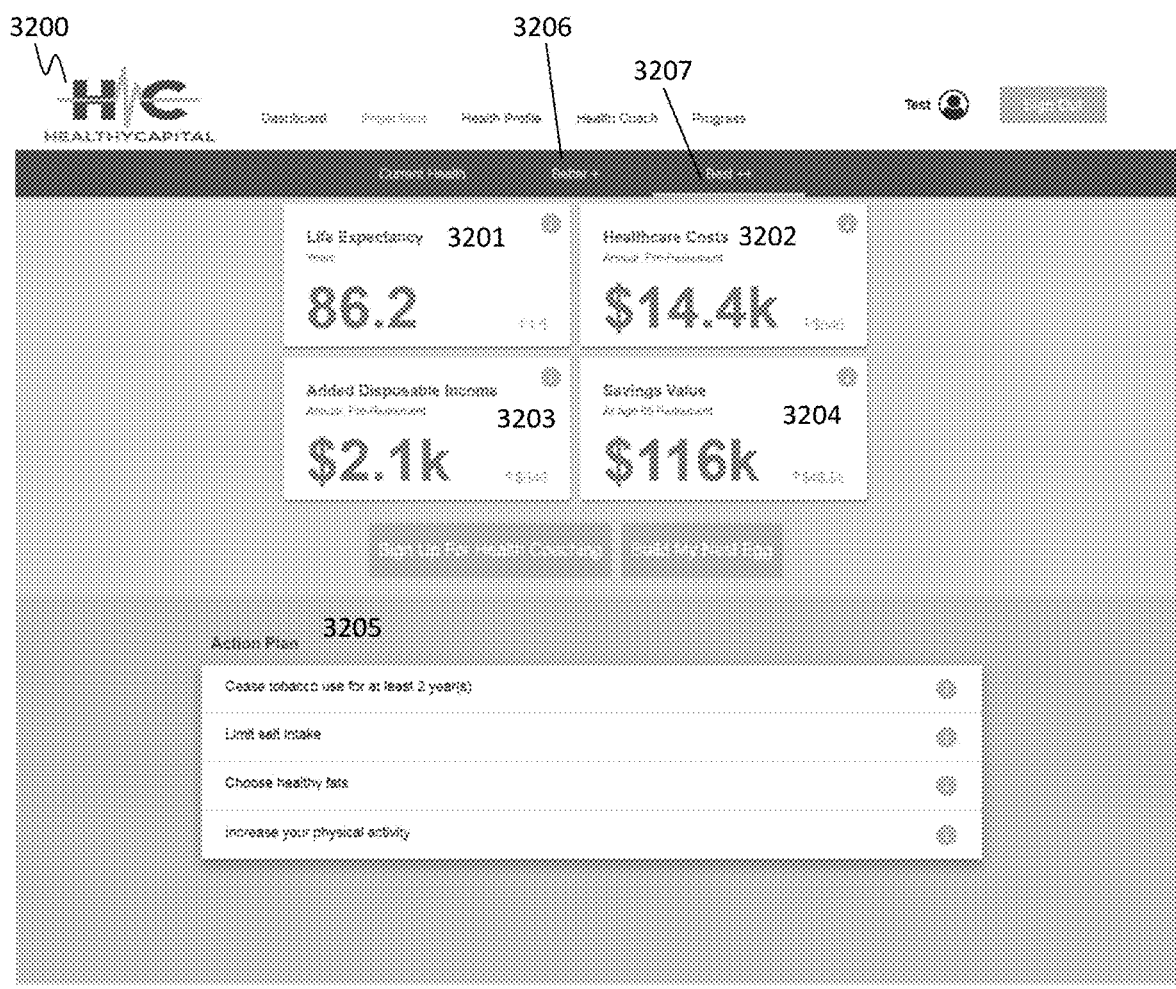
FIG. 32 depicts health and healthcare cost projections based on best potential behavior modifications in accordance with an embodiment.

Referring to FIGS. 31 and 32, embodiments are shown where a user has selected the "better" 3106 and "best" 3107 options, respectively. Accordingly, the system may, in some embodiments, update the user interface 3100/3200 to display projections of the user's life expectancy 3101/3201, healthcare costs 3102/3202, added disposable income 3103/3203, and savings value 3104/3204 if they were to perform all of the recommendations provided by the system for the better option (e.g. those listed in the action plan 3005/3105/3205). In some embodiments, the "Better" and "Best" options may utilize actuarial health cost and longevity projections based on adherence to the behavior modification suggested.

In some embodiments, if a user selects "better" 3106 or "best" 3107, the system may generate and/or provide projections of cost savings (i.e., "savings value"). In a further embodiment, the system and/or user may select an age and/or preference to determine how the dollar values are calculated (e.g., the calculations could be a dollar value at age 65 (i.e., general retirement age). Accordingly, the system may show an amount or hypothetical savings balance based on a pre-determined rate of return being applied to one or all potential invested cost savings, which are associated with these behavior medications, as discussed herein.

Figure 33:
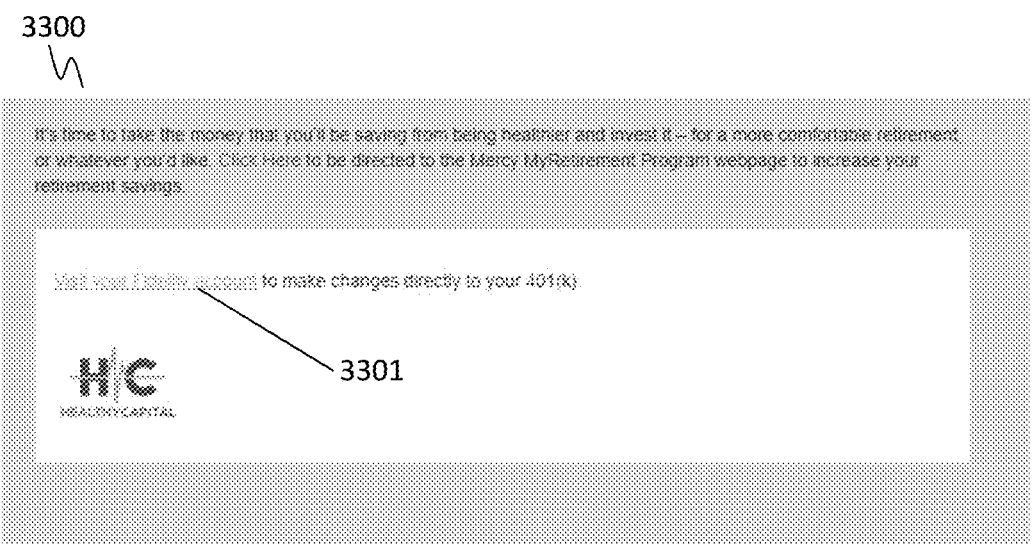
FIG. 33 depicts investment assistance based on the healthcare cost projections in accordance with an embodiment.

In an additional embodiment, the system may offer investment suggestions or may allow a user to associate their personal retirement/investment account with their user profile. Accordingly, in some embodiments, the system may, as shown in FIG. 33, prompt the user to access their pre-registered, or known, savings account 3301 directly from the website user interface 3300.

Figure 34:
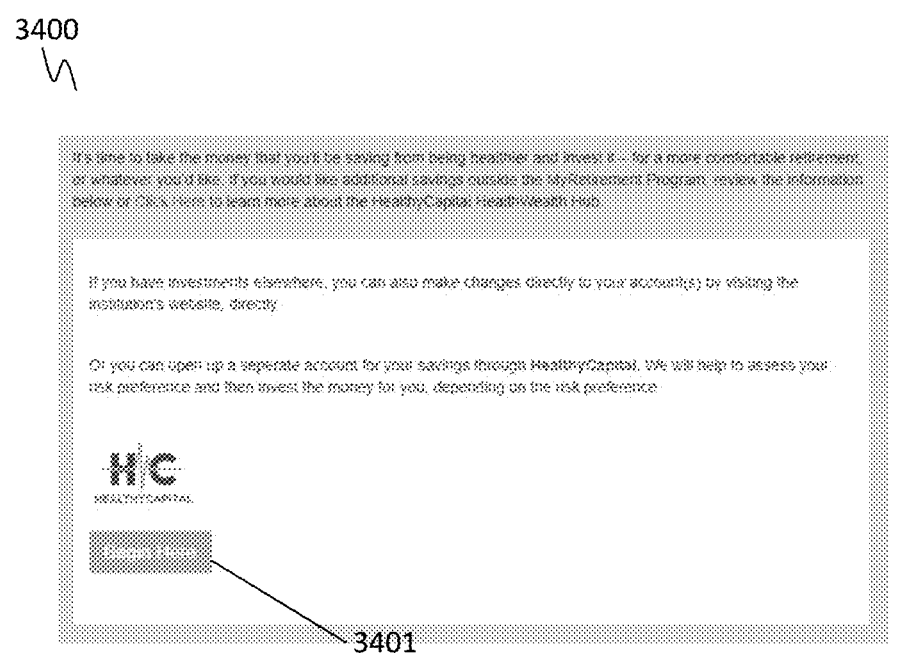

Referring now to FIG. 34, an alternative embodiment is shown, in which the user has not previously registered an investment account. Accordingly, the system may display on a user interface 3400 an option to open a new retirement account and/or register an existing account with the system. Thus, a user may click "begin here" 3401 within the user interface 3400 to being the process of further investment.

A illustrative example embodiment user interface 3500 is shown in FIG. 35, which allows a user enter in various information (i.e., a risk assessment questionnaire). Various non-limiting examples of such input may comprise a financial goal 3501, investment knowledge 3502, investment experience 3503, current investment term 3504, tolerance for risk 3505, date of planned withdrawal 3506, financial security level 3507, etc. In a further embodiment, the system may also gather information (e.g., financial, geographical, historical, political, geo-political, etc.) to better determine an investment strategy.

Figure 36:
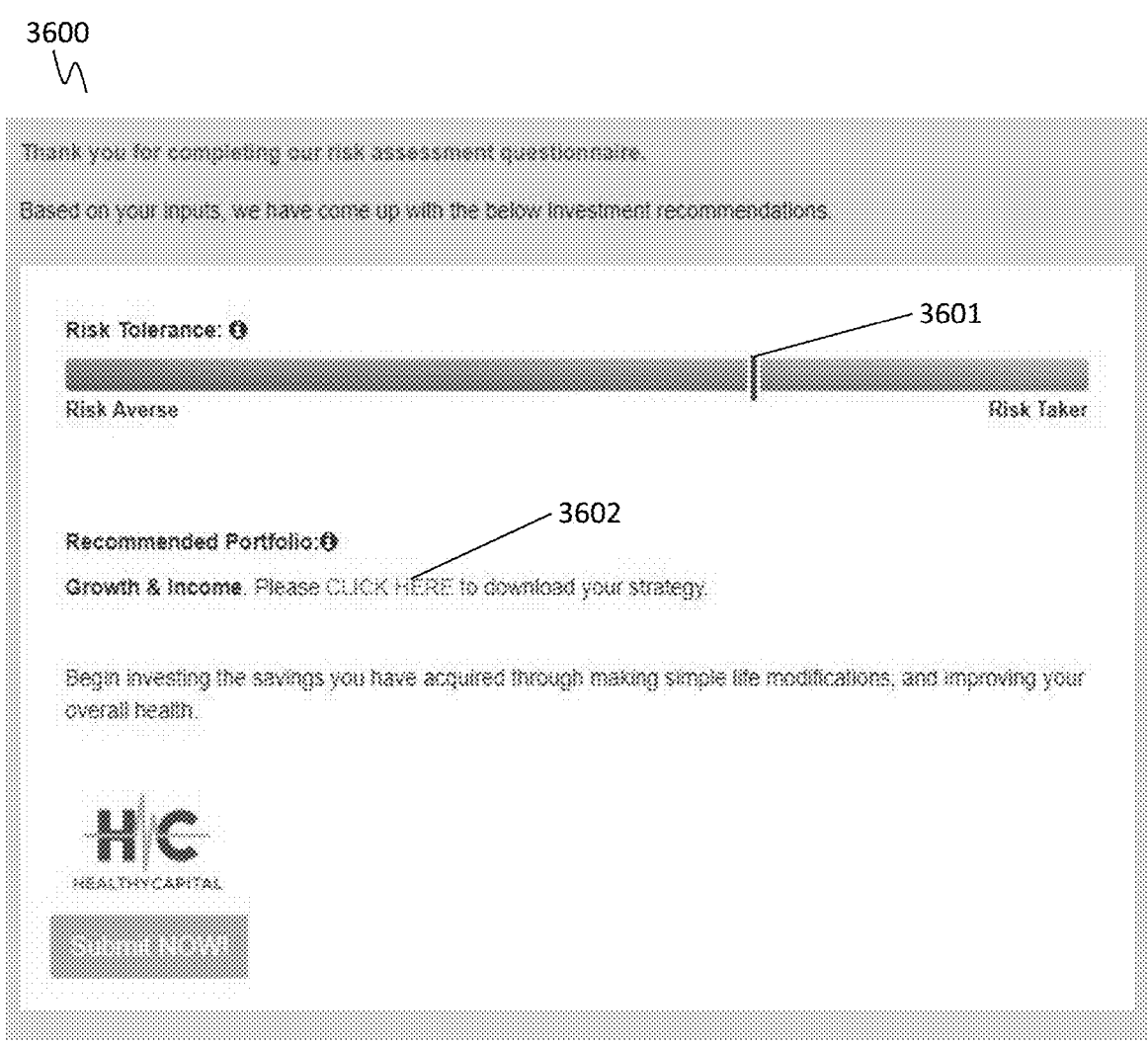
FIG. 36 depicts investment assistance based on the healthcare cost projections in accordance with another embodiment.
Figure 37:
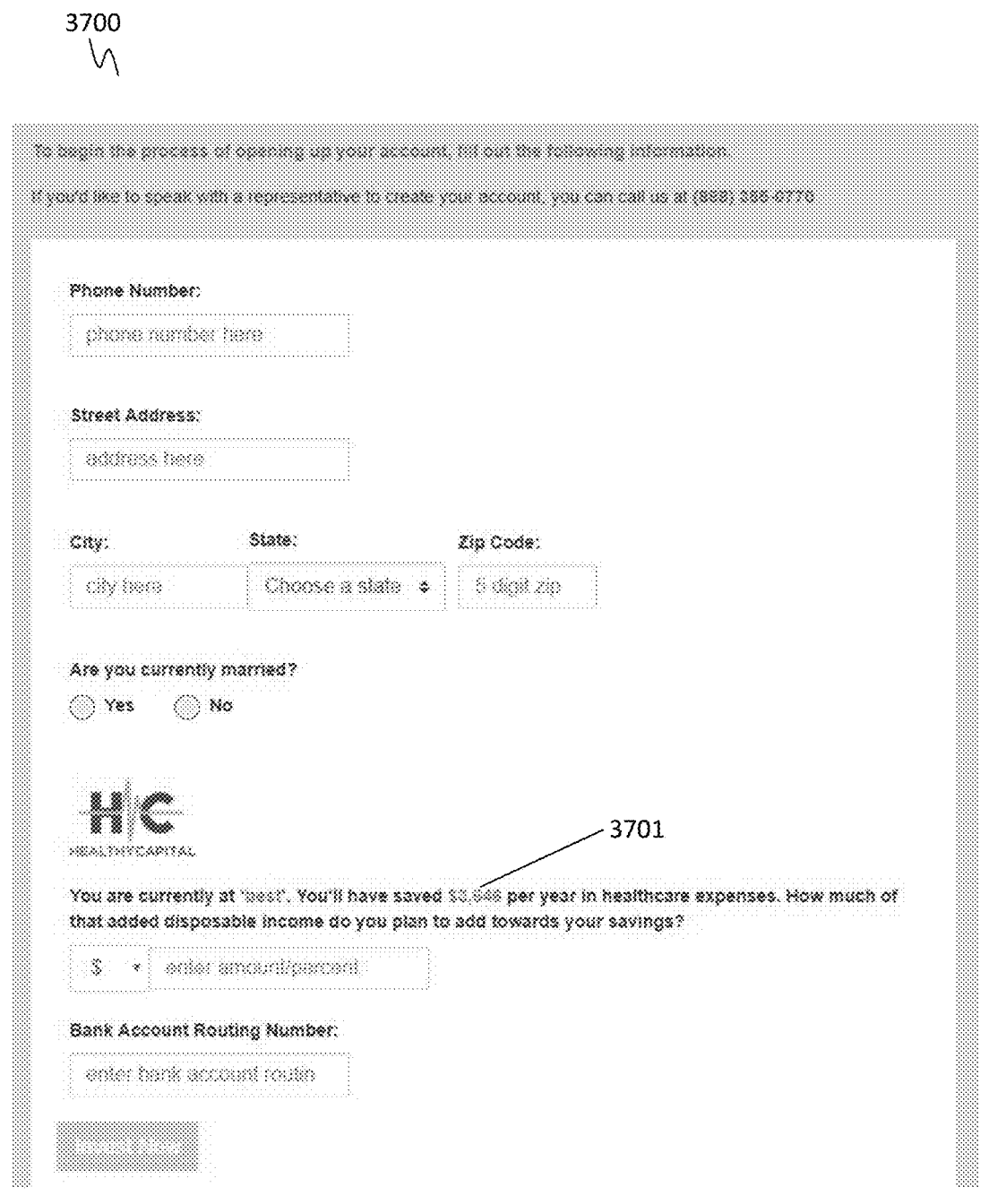

Referring now to FIG. 36, a risk tolerance assessment interface 3600 is prepared and/or delivered to the user (e.g., via the user interface, email, mobile notification, etc.). In some embodiments, and as shown, the system may display the determined user risk tolerance 3601 (e.g., as a numerical value, on a sliding scale, as a color scale, etc.). In a further embodiment, the system may also generate a total investment strategy report and make it available via the user interface 3602. Referring briefly to FIG. 37, if a user decides to accept the system's recommendations, they may then be directed to a new user interface within which to register for an investment account and/or select how much of the savings 3701

Figure 38:
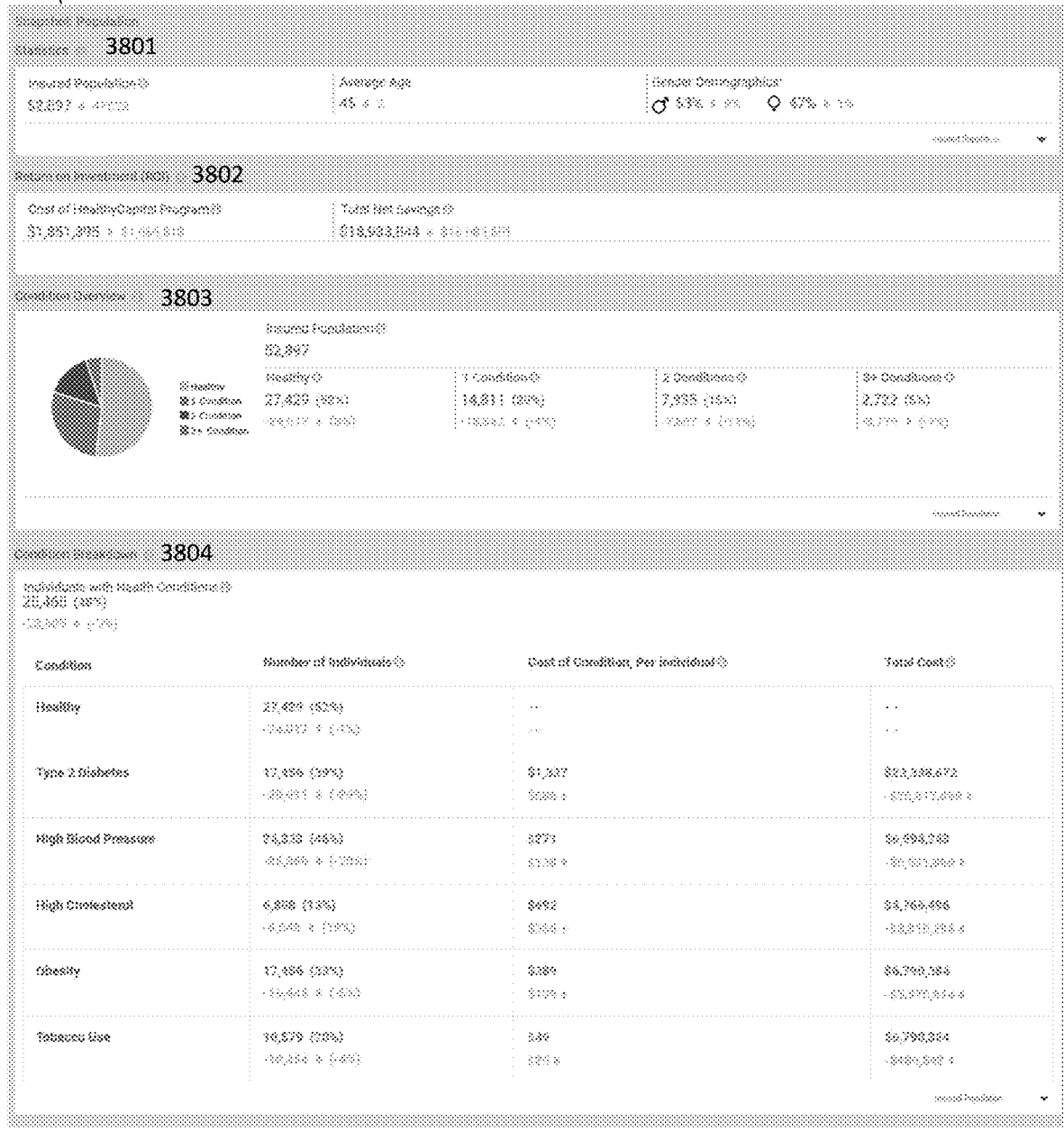
FIG. 38 depicts an administrative data overview in accordance with an embodiment.
Figure 39:
FIG. 39 depicts a continuation of an administrative data overview in accordance with an embodiment.

Referring now to FIGS. 38 and 39, an illustrative example of an administrative panel 3800/3900 is shown. Displayed data may comprise a statistical overview 3801, a return on investment 3302 for using the system, a health condition overview 3803, a condition breakdown 3804, a condition by age group overview 3901, an overview of the insured population 3902, and claims expenditures 3903. These tools will allow a company providing payment for or insuring users to raise user health and lower expense by providing insight into areas to emphasize or incentivize behavior modification.

Accordingly, various embodiments are disclosed herein, that unlike traditional systems, can show the benefit of adopting a small number of protocols that result in an increase in life expectancy as well as lowered costs though the user input and claims data.

Figure 40:
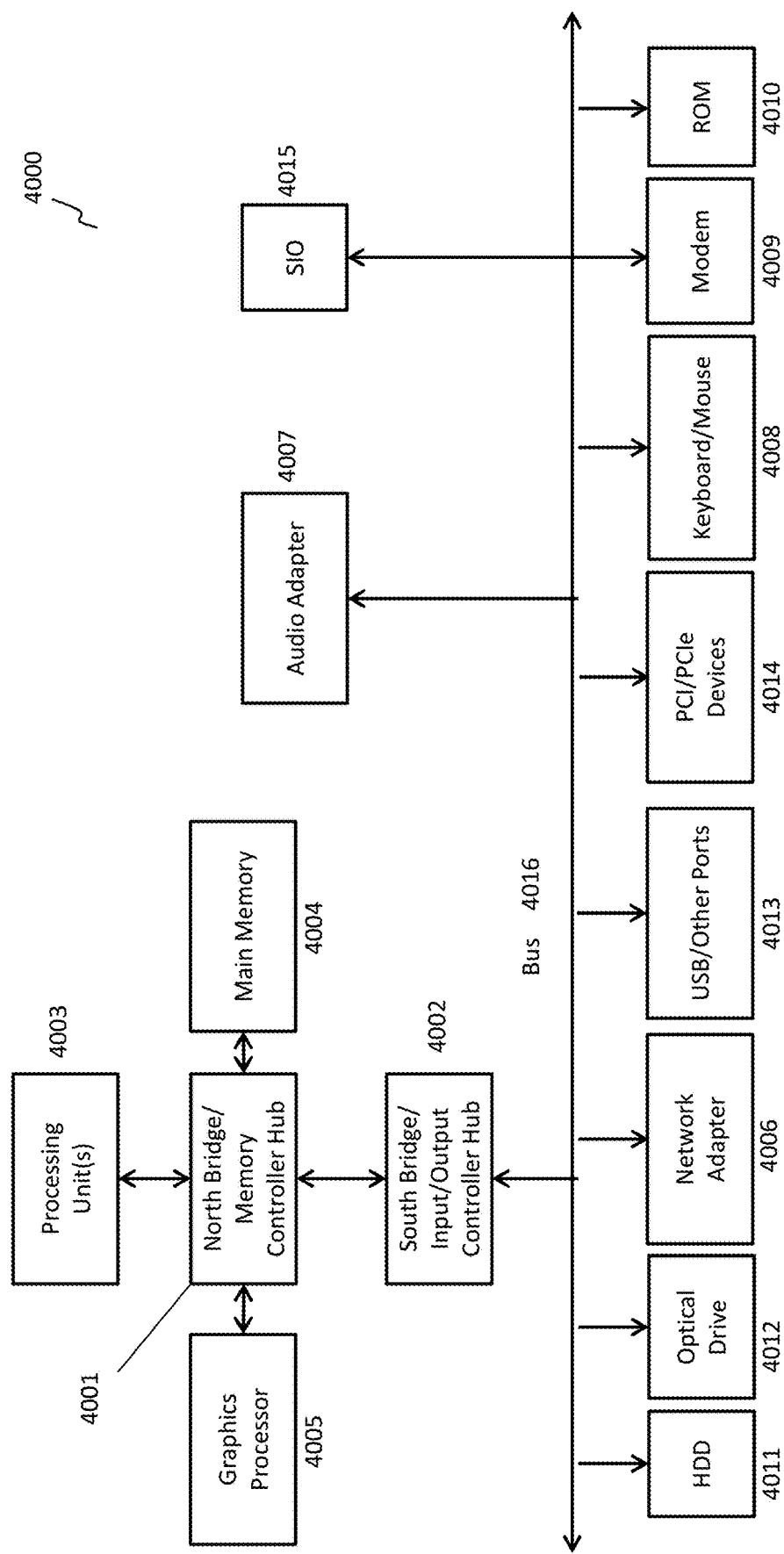
FIG. 40 depicts a block diagram of an illustrative data processing system in accordance with an embodiment.

FIG. 40 illustrates a block diagram of an illustrative data processing system 4000 in which aspects of the illustrative embodiments are implemented. The data processing system 4000 is an example of a computer, such as a server or client, in which computer usable code or instructions implementing the process for illustrative embodiments of the present invention are located. In some embodiments, the data processing system 4000 may be a server computing device. For example, the data processing system 4000 can be implemented in a server or another similar computing device. The data processing system 4000 can be configured to, for example, transmit and receive user information.

In the depicted example, data processing system 4000 can employ a hub architecture including a north bridge and memory controller hub (NB/MCH) 4001 and south bridge and input/output (I/O) controller hub (SB/ICH) 4002. Processing unit 4003, main memory 4004, and graphics processor 4005 can be connected to the NB/MCH 4001. Graphics processor 4005 can be connected to the NB/MCH 4001 through, for example, an accelerated graphics port (AGP).

In the depicted example, a network adapter 4006 connects to the SB/ICH 4002. An audio adapter 4007, keyboard and mouse adapter 4008, modem 4009, read only memory (ROM) 4010, hard disk drive (HDD) 4011, optical drive (e.g., CD or DVD) 4012, universal serial bus (USB) ports and other communication ports 4013, and PCI/PCIe devices 4014 may connect to the SB/ICH 4002 through bus system 4016. PCI/PCIe devices 4014 may include Ethernet adapters, add-in cards, and PC cards for notebook computers. ROM 4010 may be, for example, a flash basic input/output system (BIOS). The HDD 4011 and optical drive 4012 can use an integrated drive electronics (IDE) or serial advanced technology attachment (SATA) interface. A super I/O (SIO) device 4015 can be connected to the SB/ICH 4002.

An operating system can run on the processing unit 4003. The operating system can coordinate and provide control of various components within the data processing system 4000. As a client, the operating system can be a commercially available operating system. An object-oriented programming system, such as the Java™ programming system, may run in conjunction with the operating system and provide calls to the operating system from the object-oriented programs or applications executing on the data processing system 4000. As a server, the data processing system 4000 can be an IBM® eServer™ System p® running the Advanced Interactive Executive operating system or the Linux operating system. The data processing system 4000 can be a symmetric multiprocessor (SMP) system that can include a plurality of processors in the processing unit 4003. Alternatively, a single processor system may be employed.

Instructions for the operating system, the object-oriented programming system, and applications or programs are located on storage devices, such as the HDD 4011, and are loaded into the main memory 4004 for execution by the processing unit 4003. The processes for embodiments described herein can be performed by the processing unit 4003 using computer usable program code, which can be located in a memory such as, for example, main memory 4004, ROM 4010, or in one or more peripheral devices.

A bus system 4016 can be comprised of one or more busses. The bus system 4016 can be implemented using any type of communication fabric or architecture that can provide for a transfer of data between different components or devices attached to the fabric or architecture. A communication unit such as the modem 4009 or the network adapter 4006 can include one or more devices that can be used to transmit and receive data.

Those of ordinary skill in the art will appreciate that the hardware depicted in FIG. 40 may vary depending on the implementation. Other internal hardware or peripheral devices, such as flash memory, equivalent non-volatile memory, or optical disk drives may be used in addition to or in place of the hardware depicted. Moreover, the data processing system 4000 can take the form of any of a number of different data processing systems, including but not limited to, client computing devices, server computing devices, tablet computers, laptop computers, telephone or other communication devices, personal digital assistants, and the like. Essentially, data processing system 4000 can be any known or later developed data processing system without architectural limitation.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Several of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. No claim element herein is to be construed under the provisions of 35 U.S.C. 112(f) unless the element is expressly recited using the phrase "means for."

What is claimed is:

1. A system, comprising:
   a processor; and
   a non-transitory, computer-readable storage medium in operable communication with the processor, wherein the computer-readable storage medium contains one or more programming instructions that, when executed, cause the processor to:
   obtain, from a client device, client data for an individual and, from one or more databases, claim data and actuarial data;
   generate a life expectancy value and a plurality of base healthcare expense cost values based on one or more of the client data, the actuarial data, or the claim data;
   determine a plurality of cost adjustment factors based on the claim data, wherein each of the cost adjustment factors comprises a predicted future cost for one or more of the base healthcare expense cost values, and wherein at least one of the cost adjustment factors is associated with future behavior of the individual;
   generate one or more behavior modifications associated with the at least one cost adjustment factors, wherein the behavior modifications correlate to a lower predicted future cost;
   generate a medical expenses retirement savings value and a plurality of adjusted healthcare cost values based the one or more behavior modifications and at least one of the life expectancy value, the base healthcare expense cost values, the cost adjustment factors; and
   transmit, via one or more networks, to the client device, and display, within an interactive display, at least one report generated based on the medical expenses retirement savings value and the adjusted healthcare cost values,
   wherein the interactive display comprises a plurality of display elements each comprising at least one of the adjusted healthcare cost values graphically correlated with a type of healthcare expense and one or more portions of the client data, and wherein the interactive display is configured to, responsive to receiving user input identifying one of the display elements, display one or more costs based on one or more of the cost adjustment factors or behavior modifications associated with the adjusted healthcare cost in the one of the display elements.

2. The system of claim 1, wherein each of the base healthcare expense cost values comprises a cost of a healthcare expense during retirement.

3. The system of claim 1, wherein:
the cost adjustment factors comprise one or more of a condition diagnosis duration factor, a condition management regime factor, a cost trend factor, a client age factor, or a client gender factor; and
one or more of the cost adjustment factors are statistically reliable by being tested using at least 2,000 actual claims.

4. The system of claim 1, wherein the programming instructions, when executed, further cause the processor to:
receive updated information comprising at least one of a legislative change or a cost trend change; and
dynamically modify one or more of the adjusted healthcare cost values based on the updated information.

5. The system of claim 1, wherein the report comprises one or more of a financial results report or a medical expenses report comprising one or more of the medical expenses retirement savings value, the base healthcare expense cost values, or the adjusted healthcare cost values.

6. The system of claim 1, wherein the plurality of display elements comprise cells arranged in at least one row and at least one column, wherein the column is associated with the type of healthcare expense, and wherein the row is associated with the portions of the client data and a level of healthcare management.

7. The system of claim 1, wherein the interactive display further comprises multiple behavior modification options associated with the same cost adjustment factor, wherein the multiple behavior modification options are ranked according to the magnitude of the associated adjustment in healthcare costs.

8. A non-transitory computer-readable storage medium having computer-readable program code configured to, when executed by one or more processors, cause the one or more processors to:
obtain, from a client device, client data for an individual and, from one or more databases, claim data and actuarial data;
generate a life expectancy value and a plurality of base healthcare expense cost values based on one or more of the client data, the actuarial data, or the claim data;
determine a plurality of cost adjustment factors based on the claim data, wherein each of the cost adjustment factors comprises a predicted future cost for one or more of the base healthcare expense cost values, and wherein at least one of the cost adjustment factors is associated with future behavior of the individual;
generate one or more behavior modifications associated with the at least one cost adjustment factors, wherein the behavior modifications correlate to a lower predicted future cost;
generate a medical expenses retirement savings value and a plurality of adjusted healthcare cost values based the one or more behavior modifications and at least one of the life expectancy value, the base healthcare expense cost values, the cost adjustment factors; and
transmit, via one or more networks, to the client device, and display, within an interactive display, at least one report generated based on the medical expenses retirement savings value and the adjusted healthcare cost values,
wherein the interactive display comprises a plurality of display elements each comprising at least one of the adjusted healthcare cost values graphically correlated with a type of healthcare expense and one or more portions of the client data, and
wherein the interactive display is configured to, responsive to receiving user input identifying one of the display elements, display one or more costs based on one or more of the cost adjustment factors or behavior modifications associated with the adjusted healthcare cost in the one of the display elements.

9. The non-transitory computer-readable storage medium of claim 8, wherein each of the base healthcare expense cost values comprises a cost of a healthcare expense during retirement.

10. The non-transitory computer-readable storage medium of claim 8, wherein:
the cost adjustment factors comprise one or more of a condition diagnosis duration factor, a condition management regime factor, a cost trend factor, a client age factor, or a client gender factor; and
one or more of the cost adjustment factors are statistically reliable by being tested using at least 2,000 actual claims.

11. The non-transitory computer-readable storage medium of claim 8, wherein the computer-readable program code is further configured to, when executed by the one or more processors, further cause the one or more processors to:
receive updated information comprising at least one of a legislative change or a cost trend change; and
dynamically modify one or more of the adjusted healthcare cost values based on the updated information.

12. The non-transitory computer-readable storage medium of claim 8, wherein the report comprises one or more of a financial results report or a medical expenses report comprising one or more of the medical expenses retirement savings value, the base healthcare expense cost values, or the adjusted healthcare cost values.

13. The non-transitory computer-readable storage medium of claim 8, wherein the plurality of display elements comprise cells arranged in at least one row and at least one column, wherein the column is associated with the type of healthcare expense, and wherein the row is associated with the portions of the client data and a level of healthcare management.

14. The non-transitory computer-readable storage medium of claim 8, wherein the interactive display further comprises multiple behavior modification options associated with the same cost adjustment factor, wherein the multiple behavior modification options are ranked according to the magnitude of the associated adjustment in healthcare costs.

15. A method implemented by one or more financial management computing device, the method comprising:
obtaining, from a client device, client data for an individual and, from one or more databases, claim data and actuarial data;
generating a life expectancy value and a plurality of base healthcare expense cost values based on one or more of the client data, the actuarial data, or the claim data;
determining a plurality of cost adjustment factors based on the claim data, wherein each of the cost adjustment factors comprises a predicted future cost for one or more of the base healthcare expense cost values, and wherein at least one of the cost adjustment factors is associated with future behavior of the individual;

generating behavior modifications associated with the at least one cost adjustment factors, wherein the behavior modifications correlate to a lower predicted future cost;

generating a medical expenses retirement savings value and a plurality of adjusted healthcare cost values based the one or more behavior modifications and at least one of the life expectancy value, the base healthcare expense cost values, the cost adjustment factors; and transmitting, via one or more networks, to the client device, and display, within an interactive display, at least one report generated based on the medical expenses retirement savings value and the adjusted healthcare cost values, wherein the interactive display comprises a plurality of display elements each comprising at least one of the adjusted healthcare cost values and graphically correlated with a type of healthcare expense and one or more portions of the client data, and wherein the interactive display is configured to, responsive to receiving user input identifying one of the display elements, display one or more costs based on one or more of the cost adjustment factors or behavior modifications associated with the adjusted healthcare cost in the one of the display elements.

16. The method of claim 15, wherein each of the base healthcare expense cost values comprises a cost of a healthcare expense during retirement.

17. The method of claim 15, wherein:

the cost adjustment factors comprise one or more of a condition diagnosis duration factor, a condition management regime factor, a cost trend factor, a client age factor, or a client gender factor; and one or more of the cost adjustment factors are statistically reliable by being tested using at least 2,000 actual claims.

18. The method of claim 15, further comprising:

receiving updated information comprising at least one of a legislative change or a cost trend change; and dynamically modifying one or more of the adjusted healthcare cost values based on the updated information.

19. The method of claim 15, wherein the report comprises one or more of a financial results report or a medical expenses report comprising one or more of the medical expenses retirement savings value, the base healthcare expense cost values, or the adjusted healthcare cost values.

20. The method of claim 15, wherein the plurality of display elements comprise cells arranged in at least one row and at least one column, wherein the column is associated with the type of healthcare expense, and wherein the row is associated with the portions of the client data and a level of healthcare management.

21. The method of claim 15, wherein the client data comprises one or more of basic, lifestyle, or medical history characteristics.

22. The method of claim 15, wherein the claim data comprises insurance claims and costs for resolving the insurance claims.

23. The method of claim 15, wherein the interactive display further comprises multiple behavior modification options associated with the same cost adjustment factor, wherein the multiple behavior modification options are ranked according to the magnitude of the associated adjustment in healthcare costs.

* * * * *